(12) United States Patent
Xie et al.

(10) Patent No.: US 8,835,171 B2
(45) Date of Patent: Sep. 16, 2014

(54) MATERIALS AND METHODS RELATED TO SODIUM/POTASSIUM ADENOSINE TRIPHOSPHASE AND CHOLESTEROL

(75) Inventors: Zi-Jian Xie, Saline, MI (US); Yiliang Chen, Toledo, OH (US); Haojie Wang, League City, TX (US)

(73) Assignee: The University of Toledo, Toledo, OH (US)

(*) Notice: Subject to any disclaimer, the term of this patent is extended or adjusted under 35 U.S.C. 154(b) by 137 days.

(21) Appl. No.: 13/521,864

(22) PCT Filed: Jan. 13, 2011

(86) PCT No.: PCT/US2011/021127
§ 371 (c)(1),
(2), (4) Date: Aug. 2, 2012

(87) PCT Pub. No.: WO2011/088208
PCT Pub. Date: Jul. 21, 2011

(65) Prior Publication Data
US 2012/0289479 A1    Nov. 15, 2012

Related U.S. Application Data

(60) Provisional application No. 61/294,665, filed on Jan. 13, 2010.

(51) Int. Cl.
*G01N 33/92* (2006.01)
*C12Q 1/34* (2006.01)
*G01N 33/50* (2006.01)

(52) U.S. Cl.
CPC ...... *G01N 33/92* (2013.01); *C12Q 1/34* (2013.01); *G01N 33/5008* (2013.01)
USPC .............................. 435/375; 435/7.1; 435/7.4

(58) Field of Classification Search
CPC ....... C12Q 1/34; G01N 33/92; G01N 33/5008
USPC .......................................... 435/375, 7.1, 7.4
See application file for complete search history.

(56) References Cited

U.S. PATENT DOCUMENTS

| | | | |
|---|---|---|---|
| 2,698,822 A | 1/1955 | Halpern et al. |
| 3,122,475 A | 2/1964 | Schaeppi |
| 3,687,944 A | 8/1972 | Pettit et al. |
| 4,261,971 A | 4/1981 | Appelgren et al. |
| 5,153,178 A | 10/1992 | Maroko |
| 5,888,527 A | 3/1999 | Nashimoto et al. |
| 5,965,540 A | 10/1999 | Waller |
| 6,071,885 A | 6/2000 | Florkiewicz |
| 6,113,965 A | 9/2000 | Goodsall et al. |
| 6,261,760 B1 | 7/2001 | Fielding et al. |
| 6,562,864 B1 | 5/2003 | Larson |
| 6,726,935 B2 | 4/2004 | Ji et al. |
| 7,078,060 B2 | 7/2006 | Burrell et al. |
| 7,157,493 B2 | 1/2007 | Zhao et al. |
| 7,195,783 B2 | 3/2007 | Shan et al. |
| 7,402,325 B2 | 7/2008 | Addington |
| 7,858,126 B2 | 12/2010 | Singh et al. |
| 8,283,441 B2 | 10/2012 | Xie et al. |
| 8,394,434 B2 | 3/2013 | Addington et al. |
| 8,524,286 B2 | 9/2013 | Smothers |
| 2002/0039764 A1 | 4/2002 | Rosen et al. |
| 2002/0055644 A1 | 5/2002 | Winter et al. |
| 2002/0091085 A1 | 7/2002 | Kay et al. |
| 2002/0168425 A1 | 11/2002 | Nakayama et al. |
| 2004/0229275 A1 | 11/2004 | Hayden et al. |
| 2005/0026849 A1 | 2/2005 | Singh et al. |
| 2005/0271606 A1 | 12/2005 | Iwasaki et al. |
| 2006/0004002 A1 | 1/2006 | Thrash |
| 2006/0035835 A1 | 2/2006 | Taniyama et al. |
| 2006/0094772 A1 | 5/2006 | Chang et al. |
| 2006/0205679 A1 | 9/2006 | Streeper et al. |
| 2007/0092970 A1 | 4/2007 | Liang |
| 2007/0092972 A1 | 4/2007 | Xiao et al. |
| 2007/0098765 A1 | 5/2007 | Zhao et al. |
| 2007/0161589 A1 | 7/2007 | Bennett et al. |
| 2008/0317878 A1 | 12/2008 | Li et al. |
| 2009/0082293 A1 | 3/2009 | Giordano et al. |
| 2009/0143279 A1 | 6/2009 | Mootha et al. |
| 2009/0226513 A1 | 9/2009 | Xie et al. |

(Continued)

FOREIGN PATENT DOCUMENTS

| | | |
|---|---|---|
| CN | 101374571 A | 2/2009 |
| CN | 101541319 A | 9/2009 |
| WO | 97/34482 A1 | 9/1997 |
| WO | 02/14343 A1 | 2/2002 |
| WO | 02/092573 A2 | 11/2002 |
| WO | 03/016475 A2 | 2/2003 |
| WO | 2004/004785 A1 | 1/2004 |
| WO | 2004/043384 A2 | 5/2004 |
| WO | 2007/023011 A2 | 3/2007 |
| WO | 2007/089688 A2 | 8/2007 |

(Continued)

OTHER PUBLICATIONS

European Search Report, Application No. 0776299.6 dated Aug. 18, 2009.
Chen, Y., "The N-Terminus of a1 Subunit and Na/K-ATPase-Mediated Signal Transduction," Final Approval of Dissertation, The University of Toledo, College of Medicine, 2009.
Liang, M. et al., "Functional Characterization of Src-lnteracting Na/K—ATPase Using RNA Interference Assay," The Journal of Biological Chemistry, Jul. 2006, pp. 19709-19719, vol. 281, No. 28.

(Continued)

*Primary Examiner* — Brandon Fetterolf
*Assistant Examiner* — Yih-Horng Shiao
(74) *Attorney, Agent, or Firm* — MacMillan, Sobanski & Todd, LLC

(57) ABSTRACT

This invention is based in part on the elucidation of new structural conformations and functions of the sodium/potassium adenosine triphosphate synthase (Na/K ATPase), and especially elucidation of new binding sites and interactions. The present invention provides practical applications of several surprising structural and functional relationships between Na/K ATPase and compounds which interact with Na/K ATPase. Disclosure of these structures and relationships provides insight and practical solutions to chemically affecting not only the Na/K ATPase interactions, but also regulators known to be upstream and downstream.

15 Claims, 10 Drawing Sheets

(7 of 10 Drawing Sheet(s) Filed in Color)

(56) References Cited

U.S. PATENT DOCUMENTS

| | | |
|---|---|---|
| 2010/0056446 A1 | 3/2010 | Xie et al. |
| 2010/0092585 A1 | 4/2010 | Smothers |
| 2011/0245167 A1 | 10/2011 | Xie et al. |
| 2012/0302630 A1 | 11/2012 | Xie et al. |
| 2013/0011335 A1 | 1/2013 | Xie et al. |

FOREIGN PATENT DOCUMENTS

| | | |
|---|---|---|
| WO | 2008/054792 A2 | 5/2008 |
| WO | 2010/053771 A1 | 5/2010 |
| WO | 2010/071767 A2 | 6/2010 |
| WO | 2010/071767 A3 | 6/2010 |
| WO | 2011/034772 A1 | 3/2011 |
| WO | 2011/088208 A1 | 7/2011 |
| WO | 2011/088210 A1 | 7/2011 |

OTHER PUBLICATIONS

Sato, A. et al., "α-Mangostin Induces Ca2+—ATPase-Dependent Apoptosis via Mitochondrial Pathway in PC12 Cells," Journal of Pharmacological Sciences, 2004, pp. 33-40, vol. 95.
Tian, J. et al., "Na/K-ATPase Moonlights via Ouabine-Regulated Interaction with Src," Abstract, The FASEB Journal, Mar. 2004, vol. 18, No. 5.
Townsend, P.A. et al., "Epigallocatechin-3-Gallate Inhibits STAT-1 Activation and Protects Cardiac Myocytes from Ischemia/Reperfusion-Induced Apoptosis," The FASEB Journal, 2004, doi: 10.1096/fj.04-1716fje.
Zhang, Z. et al., "Identification of Hyroxyxanthones as Na/K-ATPase Ligands," Molecular Pharmacology, 2010, pp. 961-967, vol. 77, No. 6.
Canadian Notice of Requisition by the Examiner, Application No. 2,667,251, dated Dec. 13, 2013.
Chinese 1st Office Action, Application No. 201180010298.9, dated Aug. 16, 2013.
Chinese 2nd Office Action, Application No. 200980149736.2, dated Oct. 15, 2013.
Chinese 3rd Office Action, Application No. 200780043725.7, dated Jun. 12, 2012.
Chinese 4th Office Action, Application No. 200780043725.7, dated Nov. 15, 2012.
Chinese First Office Action, Application No. 200780003862.8, dated Jun. 30, 2011.
Chinese First Office Action, Application No. 201180010295.5, dated May 22, 2013.
Chinese Notification of the First Office Action, Appln. No. 201080046743.2, dated Apr. 25, 2013.
Chinese Office Action, Application No. 200980149736.2 dated Nov. 28, 2012.
Chinese Office Action, Application No. 200780043725.7 dated Jan. 12, 2011.
Chinese Second Office Action, Application No. 200780043725.7, dated Nov. 16, 2011.
Chinese Second Office Action, Application No. 201180010295.5, dated Jan. 13, 2014.
EP Communication, Application No. 10817681.9, dated Mar. 7, 2013.
EP Communication, Application No. 10817681.9, dated Feb. 26, 2014.
EP Communication, Application No. 07867328.2, dated Nov. 6, 2013.
EP Communication, Application No. 07762999.6, dated Aug. 18, 2009.
European Supplementary Search Report, Application No. 07762999.6 dated Sep. 4, 2009.
PCT International Preliminary Report on Patentability, PCT/US07/002365 filed Jan. 30, 2007, dated Aug. 5, 2008.
PCT International Preliminary Report on Patentability, PCT/US2009/062317 filed Oct. 28, 2009, dated May 12, 2011.
PCT International Preliminary Report on Patentability, PCT/US09/067845 filed Dec. 14, 2009, dated Jun. 23, 2011.
PCT International Preliminary Report on Patentability, PCT/US07/023011 filed Oct. 31, 2007, dated May 14, 2009.
PCT International Search Report and the Written Opinion, PCT/US09/62317 filed Oct. 28, 2009, dated Mar. 2, 2010.
PCT International Search Report and the Written Opinion, PCT/US09/67845 filed Dec. 14, 2009, dated Aug. 10, 2010.
PCT International Search Report and the Written Opinion, PCT/US07/23011 filed Oct. 31, 2007, dated Sep. 26, 2008.
PCT International Search Report and the Written Opinion, PCT/US11/21130 filed Jan. 13, 2011, dated Jun. 7, 2011.
PCT International Search Report and the Written Opinion, PCT/US11/21127 filed Jan. 13, 2011, dated Apr. 13, 2011.
PCT International Search Report and the Written Opinion, PCT/US07/02365 filed Jan. 30, 2007, dated Dec. 20, 2007.
PCT International Search Report and the Written Opinion, PCT/US10/48227 filed Sep. 9, 2010, dated Nov. 8, 2010.
PCT International Search Report and Written Opinion, Application No. 2013/040181, dated Oct. 25, 2013.
Amigo, L. et al., "Enrichment of Canalicular Membrane with Cholesterol and Sphingomyelin Prevents Bile Salt-Induced Hepatic Damage," Journal of Lipid Research, 1999, pp. 533-542, vol. 40.
Aydemir-Koksoy, A. et al., "Ouabain-Induced Signaling and Vascular Smooth Muscle Cell Proliferation," The Journal of Biological Chemistry, 2001, pp. 46605-46611, vol. 276, No. 49.
Bork, "Powers and Pitfalls in Sequence Analysis: The 70% Hurdle", Genome Research, 2000, 10, pp. 398-400.
Brenner, "Errors in Genome Annotation", Trends in Genetics, 1999, 15(4), pp. 132-133.
Cai, T. et al., "Regulation of Caveolin-1 Membrane Trafficking by the Na/K-ATPase," Journal of Cell Biology, 2008, pp. 1153-1169, vol. 182, No. 6.
Chan, et al., Interactions between traditional Chinese medicines and Western therapeutics, Current Opinion in Drug Discovery & Development, 2010, 13 (1), pp. 50-65.
Chen, Y. et al., "Regulation of Intracellular Cholesterol Distribution by Na/K-ATPase," The Journal of Biological Chemistry, May 2009, pp. 14881-14890, vol. 284, No. 22.
Chen, Y., "The N-Terminus of a1 Subunit and Na/K—ATPase-Mediated Signal Transduction," Final Approval of Dissertation, The University of Toledo, College of Medicine, 2009.
Cooper, R. et al., "Medicinal Benefits of Green Tea: Part I. Review of Noncancer Health Benefits," The Journal of Alternative and Complementary Medicine, 2005, pp. 521-528, vol. 11, No. 3.
Cruz, J.C. et al., "Role of Niemann-Pick Type C1 Protein in Intracellular Trafficking of Low Density Lipoprotein-Derived Cholesterol," The Journal of Biological Chemistry, 2000, pp. 4013-4021, vol. 275, No. 6.
Darra, E. et al., "Protective Effect of Epigallocatechin-3-Gallate on Ischemia/Reperfusion-Induced Injuries in the Heart: STAT1 Silencing Flavenoid," Genes Nutr., 2007, pp. 307-310, vol. 2.
Dmitrieva, R.I. et al., "Cardiotonic Steroids: Potential Endogenous Sodium Pump Ligands with Diverse Function," Exp. Biol. Med., 2002, pp. 561-569, vol. 227, No. 8.
Doerks, et al., "Protein Annotation: Detective Work for Function Prediction", Trends in Genetics, 1998, 14(6), pp. 248-250.
Donovan, et al., The Effect of Age on Digitoxin Pharmacokinetics, Br. J. Clin. Pharmac., 1981.
Elkareh, J. et al., "Marinobufagenin Stimulates Fibroblast Collagen Production and Causes Fibrosis in Experimental Uremic Cardiomyopathy," Hypertension, 2007, pp. 215-224, vol. 49.
El-Okdi, N. et al., "Effects of Cardiotonic Steroids on Dermal Collagen Synthesis and Wound Healing," J. Appl. Physiol., 2008, pp. 30-36, vol. 105.
Haas, M. et al., "SRC-Mediated Inter-Receptor Cross-Talk Between the Na+/K+-ATPase and the Epidermal Growth Factor Receptor Relays the Signal from Ouabain to Mitogen-Activated Protein Kinases," The Journal of Biological Chemistry, 2002, pp. 18694-18702, vol. 277, No. 21.

(56) References Cited

OTHER PUBLICATIONS

Hotta, Y. et al., "Positive Inotropic Effect of Purified Green Tea Catechin Derivative in Guinea Pig Hearts: The Measurements of Cellular Ca2+ and Nitric Oxide Release," European Journal of Pharmacology, 2006, pp. 123-130, vol. 552.

Ignatushchenko, et al., Xanthones As Antimalarial Agents: Stage Specificity, Am. J. Trop. Med. Hyg., 62 (1) 2000, pp. 77-81.

Ikeda, I. et al., "Tea Catechins with a Galloyl Moiety Suppress Postprandial Hypertriacylglycerolemia by Delaying Lymphatic Transport of Dietary Fat in Rats," The Journal of Nutrition, 2005, pp. 155-159, vol. 135.

Kabat, M.M. et al., "Cardiotonic Steroids. 5. A Synthesis of Bufadienolides and Cardenolides from 3β-Acetoxy-5-Androsten-17-One via Common Intermediates," J. Org. Chem., 1983, pp. 4248-4251, vol. 48.

Katz, B. et al., "Controlled-Release Drug Delivery Systems in Cardiovascular Medicine," American Heart Journal, 1995, pp. 359-368, vol. 129, No. 2.

Kennedy, D.J. et al., "Central Role for the Cardiotonic Steroid Marinobufagenin in the Pathogenesis of Experimental Uremic Cardiomyopathy," Hypertension, 2006, pp. 488-495, vol. 47.

Khundmiri, S.J. et al., "Ouabain Induces Cell Proliferation through Calcium-Dependent Phosphorylation of Akt (Protein Kinase B) in Opossum Kidney Proximal Tubule Cells," Am. J. Physiol. Cell Physiol., 2006, pp. C1247-C1257, vol. 291.

Kubota, Y. et al., "Safety of Dietary Supplements; Chronotropic and Inotropic Effects on Isolated Rat Atria," Biol. Pharm Bull., 2002, pp. 197-200, vol. 25, No. 2.

Laird, A.D. et al., "Src Family Kinase Activity is Required for Signal Tranducer and Activator of Transcription 3 and Focal Adhesion Kinase Phosphorylation and Vascular Endothelial Growth Factor Signaling in Vivo and for Anchorage-Dependent and-Independent Growth of Human Tumor Cells," Molecular Cancer Therapeutics, May 2003, pp. 461-469, vol. 2.

Lefranc, F. et al., "Targeting the α1 Subunit of the Sodium Pump to Combat Glioblastoma Cells," Neurosurgery, Jan. 2008, pp. 211-222, vol. 62, No. 1.

Liang, M. et al., "Functional Characterization of Src-lnteracting Na/K-ATPase Using RNA Interference Assay," The Journal of Biological Chemistry, Jul. 2006, pp. 19709-19719, vol. 281, No. 28.

Melero, et al., A Short Review on Cardiotonic Steriods and Their Aminoguanidine Analogues, Molecules 2000, 5, pp. 51-81.

Newman, R.A. et al., "Cardiac Glycosides as Novel Cancer Therapeutic Agents," Molecular Interventions, Feb. 2008, pp. 36-49, vol. 8, Issue 1.

Ngo, et al., Computational Complexity Protein Structure Prediction, and the Levinthal Paradox, Chapter 14, 1994, pp. 433-440 and 492-495 only.

Paquay, J.B.G. et al., "Protection Against Nitric Oxide Toxicity by Tea," J. Agric. Food Chem., 2000, pp. 5768-5772, vol. 48.

Pedro, et al., Xanthones as Inhibitors of Growth of Human Cancer Cell Lines and Their Effects on the Proliferation of Human Lymphocytes in Vitro, Bioorganic & Medicinal Chemistry 2002, 10, pp. 3725-3730.

Robia, S.L. et al., "Localization and Kinetics of Protein Kinase C-Epsilon Anchoring in Cardiac Myocytes," Biophysical Journal, May 2001, pp. 2140-2151, vol. 80.

Sato, A. et al., "α-Mangostin Induces Ca2+-ATPase-Dependent Apoptosis via Mitochondrial Pathway in PC12 Cells," Journal of Pharmacological Sciences, 2004, pp. 33-40, vol. 95.

Skolnick, et al., From Genes to Protein Structure and Function: Novel Applications of Computational Approaches in the Genomic Era, Trends in Biotech, 2000, 18(1), pp. 34-39.

Susa, M. et al., "Src Inhibitors: Drugs for the Treatment of Osteoporosis, Cancer or Both?" TiPS, 2000, pp. 489-495, vol. 21.

Tian, J. et al., "Binding of Src to Na+/K+ATPase Forms a Functional Signaling Complex," Molecualr Biology of the Cell, Jan. 2006, pp. 317-326, vol. 17.

Tian, J. et al., "Changes in Sodium Pump Expression Dictate the Effect s of Ouabine on Cell Growth," The Journal of Biological Chemistry, May 2009, pp. 14921-14929, vol. 284, No. 22.

Tian, J. et al., "Na/K—ATPase Moonlights via Ouabine-Regulated Interaction with Src," Abstract, The FASEB Journal, Mar. 2004, vol. 18, No. 5.

Townsend, P.A. et al., "Epigallocatechin-3-Gallate Inhibits STAT-1 Activation and Protects Cardiac Myocytes from Ischemia/Reperfusion-Induced Apoptosis," The FASEB Journal, 2004, doi: 0.1096/fj.04-1716fje.

Urano, Y. et al., "Transport of LDL-Derived Cholesterol from the NPC1 Compartment to the ER Involves the Trans-Golgi Network and the SNARE Protein Complex," PNAS, Oct. 2008, pp. 16513-16518, vol. 105, No. 43.

Wang, H., "Na+/K+ATPase and Signal Transduction," Final Approval of Dissertation, The University of Toledo, College of Medicine, 2005.

Wells, Additivity of Mutational Effects in Proteins, Biochemisty, 1990, vol. 29, No. 37, pp. 8509-8517.

Yang, et al., Cardiac glycosides inhibit TNF-a/Nf-kB signaling by blocking recruitment of TNF receptor-associated death domain to the TNF receptor, PNAS, Jul. 5, 2005, vol. 102, No. 27, pp. 9631-9636.

Zhang, Z. et al., "Identification of Hyroxyxanthones as Na/K—ATPase Ligands," Molecular Pharmacology, 2010, pp. 961-967, vol. 77, No. 6.

Zhong, et al., 3,4,5,6,-Tetrahydroxyxanthone Protects Against Myocardial Ischemia-Reperfusion Injury in Rats, Cardiovascular Drugs and Therapy, 2004, 18, pp. 279-288.

MATERIALS AND METHODS RELATED TO SODIUM/POTASSIUM ADENOSINE TRIPHOSPHASE AND CHOLESTEROL

CROSS-REFERENCE TO RELATED APPLICATIONS

This application claims the benefit of PCT application No. PCT/US2011/021127 filed Jan. 13, 2011 which claims priority to U.S. Provisional Application Ser. No. 61/294,665 filed on Jan. 13, 2010, the entire disclosure of which is expressly incorporated herein by reference.

STATEMENT REGARDING FEDERALLY SPONSORED RESEARCH

This invention was made with government support under Grant Numbers HL-36573 and HL-67963 awarded by the National Institutes of Health. The government has certain rights in the invention.

SEQUENCE LISTING

The instant application contains a Sequence Listing which has been submitted via EFS-web and is hereby incorporated by reference in its entirety. The ASCII copy, created on Aug. 30, 2013, is named 420_51488_SEQ_LIST_D2010-26.txt, and is 1,000 bytes in size.

BRIEF DESCRIPTION OF THE SEQUENCE LISTING

SEQ ID NO: 1 is the amino acid sequence: STNCV EGTAR GIVVY TGD.

SEQ ID NO: 2 is the CRAC amino acid sequence: LDELH RKYGT DLSRG LT.

FIELD OF THE INVENTION

This invention pertains to the field of biology, chemistry and medicine. The invention specifically pertains to ion transport proteins, small pharmaco-active molecules, research tools, diagnostics, kits and treatments related to cardiovascular diseases. Cardiotonic steroid antagonists and compositions affecting cholesterol-mediated cardiovascular disease are within the field of the invention. Other fields, such as physics and biochemistry also provide a framework for the present invention.

BACKGROUND OF THE INVENTION

This invention is based in part on the elucidation of new structural conformations and functions of the sodium/potassium adenosine triphosphate synthase (Na/K ATPase), and especially elucidation of new binding sites and interactions. The present invention provides applications of surprising structural and functional relationships between Na/K ATPase and compounds which interact with Na/K ATPase. The invention provides solutions to chemically affecting not only the Na/K ATPase interactions, but also regulators known to be upstream and downstream.

The Na/K-ATPase was originally discovered as an active ion transporter residing in the plasma membrane. The functional Na/K-ATPase is mainly consisted of α and β subunits. The a subunit is the catalytic subunit for it contains both ligand and nucleotide binding sites. Despite of its long reputation as an ion transporter, recent studies have revealed that the Na/K-ATPase, in addition to its ion pumping function, is capable of performing various other functions. For example, it was discovered that the Na/K-ATPase interacted with the Src kinase forming a functional signaling complex capable of transducing extracellular signals into activation of intracellular kinase cascades. Interestingly, the signaling Na/K-ATPase was demonstrated to mainly localize in the specialized plasma membrane microdomains called caveolae ("little caves") and interact with caveolae marker, caveolin-1 protein. The caveolin-1 protein is an ~22-kD protein mainly localized in the plasma membrane. In addition to its role in biogenesis of caveolae, it is known to play a role in cellular cholesterol homeostasis. It has been demonstrated to bind to cholesterol in a 1:1 ratio and involved in the trafficking of cholesterol between the plasma membrane and intracellular organelles. Furthermore, depletion of cellular cholesterol leads to redistribution of caveolin-1 to perinuclear regions. On the other hand, the Na/K-ATPase regulated the membrane trafficking of caveolin-1. Graded knockdown of the Na/K-ATPase α1 led to mobilization of caveolin-1 within caveolae domain and redistribution of caveolin-1 to perinuclear regions. Depletion of cellular cholesterol redistributed the Na/K-ATPase α1 out of caveolae.

SUMMARY OF THE INVENTION

In other broad embodiments, there are provided methods to identify test compositions capable of modulating intracellular cholesterol concentration, comprising: a. contacting a test composition with Na/K ATPase in a cholesterol-trafficking test model; and b. identifying if step a. results in a modulation of intracellular cholesterol concentration.

Also provided are methods to identify test compositions capable of modulating plasma membrane cholesterol concentration, comprising: a. contacting a test composition with Na/K ATPase in a cholesterol-trafficking test model; and b. identifying if step a. results in a modulation of plasma membrane cholesterol concentration. Preferred are any of the above claims, wherein modulation is a decrease in intracellular cholesterol concentration, wherein the test model is a cell culture, wherein the test model is a mammal, wherein the test model is selected from the group consisting of: liver cells; kidney cells; brain cells; nerve cells; pancreatic cells; lung cells; skin cells; heart cells; rodent cells; human cells; a mouse; a rat; a guinea pig; a dog; a monkey; and a human, wherein the test model is selected from a test model of the group consisting of: a NPC1 disease; pathogenic lipid accumulation; vascular disease; heart attack; stroke; overweight; obesity; diabetes; metabolic syndrome; thyroid malfunction; medication side effect; arthrosclerosis; heart failure; heart disease; Alzheimer's disease; Parkinson disease; Huntington disease; Tay Sachs disease; and neurodegenerative disease.

The present invention provides composition of matter comprising an amino acid compound comprising at least ten consecutive amino acid residues of the sequence LDELH RKYGT DLSRG LT [SEQ ID NO:2], or conservative substitutions of the at least ten consecutive amino acid residues, wherein the compound is capable of binding the cholesterol. Preferred are those compositions, which further comprise a therapeutically acceptable excipient. Most preferred are those wherein the amino acid compound comprises the sequence LDELH RKYGT DLSRG LT [SEQ ID NO: 2].

Also provided are methods identify test compositions capable of modulating cholesterol concentration, comprising: a. contacting a test composition with Na/K ATPase; and b. identifying if step a. results in binding to the CRAC domain of the α1 subunit of Na/K ATPase. Preferred are those methods, wherein step a. is accomplished in a manner selected from the group consisting of: in vitro and in vivo.

The present invention provides composition of matter comprising an amino acid compound comprising at least ten consecutive amino acid residues of the sequence LDELH RKYGT DLSRG LT [SEQ ID NO:2], or conservative substitutions of the at least ten consecutive amino acid residues, wherein the compound is capable of binding the cholesterol. Preferred are those compositions, which further comprise a therapeutically acceptable excipient. Most preferred are those wherein the amino acid compound comprises the sequence LDELH RKYGT DLSRG LT [SEQ ID NO: 2].

Also provided are methods to affect cholesterol transport in a cell, comprising affecting Na/K ATPase cholesterol-binding activity. Preferred are those methods, wherein Na/K ATPase cholesterol-binding activity is affected in the manner selected from the group consisting of: decreasing; increasing; eliminating; periodically disrupting; and periodically enhancing.

Also provided are methods to ameliorate neurodegeneration due to pathogenic intracellular cholesterol accumulation in an organism in need of such amelioration, comprising decreasing the cholesterol binding activity of Na/K ATPase.

Also provided are methods of treat Niemann Pick, type C1 disease, comprising decreasing the ability of Na/K ATPase to bind to cholesterol particularly, wherein the decrease is accomplished in a manner selected from the group consisting of: antagonizing the CRAC domain of the α1 subunit of Na/K ATPase; and inhibiting the CRAC domain of the α1 subunit of Na/K ATPase.

Also provided are methods to identify compositions capable of treating cholesterol-related disease states, comprising a. contacting a test composition with Na/K ATPase; and b. identifying if step a. results in antagonizing the ability of cholesterol to bind to the CRAC domain of the α1 subunit of Na/K ATPase. Preferred are those methods as described, wherein the disease state is selected from the group consisting of: NPC1; pathogenic lipid accumulation; vascular disease; heart attack; stroke; overweight; obesity; diabetes; metabolic syndrome; thyroid malfunction; medication side effect; arthrosclerosis; heart failure; heart disease; Alzheimer's disease; Parkinson disease; Huntington disease; Tay Sachs disease and neurodegenerative disease.

Also provided are methods to downregulate Na/K ATPase in a cholesterol-trafficking test model, comprising depleting plasma membrane cholesterol concentrations in the test model.

Also provided are methods to redistribute α1 subunit of Na/K ATPase to intracellular compartments in a cholesterol-trafficking test model, comprising depleting plasma membrane cholesterol concentrations in the test model.

Also provided are methods to affect the trafficking and expression of caveolin-1 in a cholesterol-trafficking test model, comprising down-regulating plasma membrane α1 subunit of Na/K ATPase.

Also provided are methods to treat NPC1 disease, comprising altering expression of the α1 subunit of Na/K ATPase so as to ameliorate the symptoms of NPC1 disease.

Various aspects of this invention will become apparent to those skilled in the art from the following detailed description of the preferred embodiment, when read in light of the accompanying drawings.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1. Acute Depletion of Membrane Cholesterol by Mβ-CD Down-regulates Na/K-ATPase α1. LLC-PK1 cells were treated with 10 mM Mβ-CD in the serum-free medium at 37° C. for 1 h, washed, and then collected after the washed cells were cultured in serum-free medium for 0, 6, and 24 h.

FIG. 3. Compound U18666A Depletes Plasma Membrane Cholesterol and Specifically Down-regulates Na/K-ATPase α1.

FIG. 4. Membrane Cholesterol Depletion Leads to Endocytosis of Na/K-ATPase α1.

FIG. 7. Down-regulation of the Na/K-ATPase α1 in Target Organs of BALB/c npc$^{nih}$/npc$^{nih}$ Mice.

DETAILED DESCRIPTION OF THE INVENTION

The inventors investigated whether cellular cholesterol depletion may lead to downregulation of the cell surface Na/K-ATPase α1, which subsequently contributes to redistribution of caveolin-1. In the present invention, the inventors demonstrate that depletion of plasma membrane cholesterol leads to endocytosis and downregulation of the Na/K-ATPase α1. Disruption of intracellular cholesterol trafficking as displayed in the Niemann-Pick type C1 (NPC1) cell phenotype is correlated with depletion of the cell surface Na/K-ATPase α1. Furthermore, the Na/K-ATPase α1 is able to interact with cholesterol directly via its N-terminus cholesterol interaction motif. The α1-cholesterol interaction affects cholesterol depletion-induced α1 downregulation. Finally, downregulation of the Na/K-ATPase α1 is demonstrated in the liver and brain of the NPC1 mouse model. Since the Na/K-ATPase is known to be involved in cell growth and survival, the present invention provides a novel explanation linking cholesterol trafficking defect to massive neurodegeneration in the NPC1 disease. The present invention provides practical applications to the discovery that the plasma membrane cholesterol regulates cell surface content of the Na/K-ATPase α1 subunit.

Depletion of Cholesterol in the Plasma Membrane Leads to Endocytosis and Reduction of the Cell Surface α1.

The reduction of α1 expression was not only observed in the in vitro cultured LLC-PK1 cells but also confirmed in vivo in the brain and hepatic cells from the NPC1 mutant mice. Interestingly, the Na/K-ATPase is known to be essential for neuronal cell growth and survival. Thus, these discoveries offer a new explanation for the molecular mechanism underlying the neurodegeneration effect in the lipid storage disorder such as NPC1 disease.

Regulation of Cell Surface Na/K-ATPase by the Plasma Membrane Cholesterol.

Cholesterol is enriched in the special plasma membrane lipid domain, caveolae. Presence of cholesterol is required for the maintenance of caveolae as cholesterol depletion leads to disruption of the caveolae structure. Moreover, decrease in cell surface cholesterol mobilizes caveolae marker caveolin-1 and redistributes it from caveolae to cytoplasm. The above cholesterol depletion effect is strikingly similar to the Na/K-ATPase α1 knockdown effect on caveolae and caveolin-1 protein. Therefore, it is proposed that cholesterol depletion may downregulate cell surface Na/K-ATPase α1, which contributes to caveolin-1 redistribution. This proposition is supported by the data in this invention.

Figure 1A:
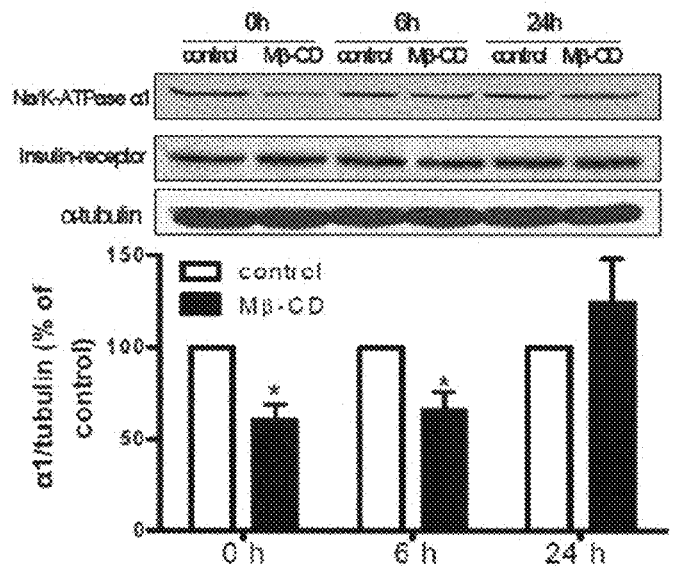
FIG. 1A. Cholesterol content in the cell lysates from different time points were measured, adjusted to protein level and compared.
Figure 1B:
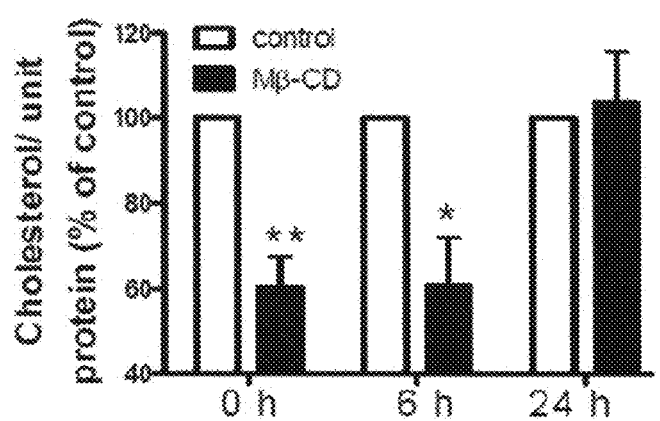
FIG. 1B. Representative Western blots are shown on the levels of Na/K-ATPase α1, insulin receptor β subunit and α-tubulin (used as loading control). Quantitative data are combined from four separate experiments and expressed as mean±SE. *, $P<0.05$.
Figure 2A:
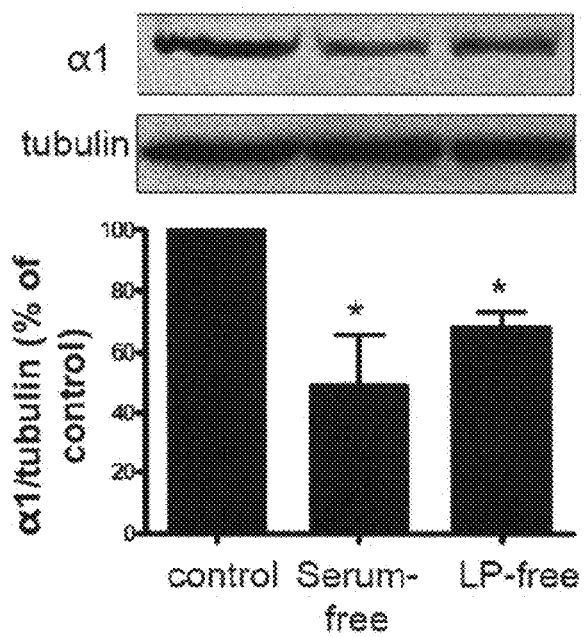
FIG. 2. Chronic Cholesterol Depletion Down-regulates Na/K-ATPase α1. LLC-PK1 Cells were cultured in DMEM plus 10% FBS (control) or 10% serum-free or 10% lipoprotein-free FBS for 48 h, lysed and measured for α1 subunit, and α-tubulin as in panel FIG. 2A and cholesterol in panel FIG. 2B. Quantitative data are combined from four separate experiments and expressed as mean±SE. *, $P<0.05$.
Figure 2B:
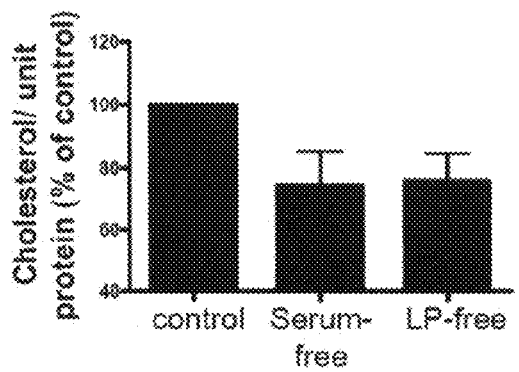
Figure 3A:
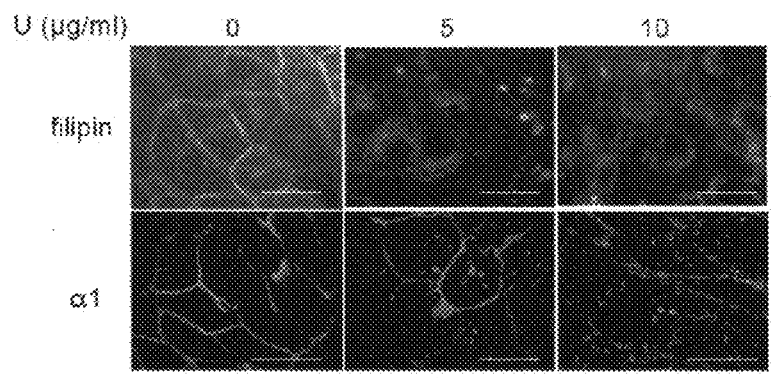
FIG. 3A. LLC-PK1 cells were treated with different doses of U18666A for 24 h, and subjected to filipin (upper panels) and α1 immunostaining (lower panels). Representative images show dose-dependent effects of U18666A compound on cellular distribution of cholesterol and Na/K-ATPase α1.
Figure 3B:
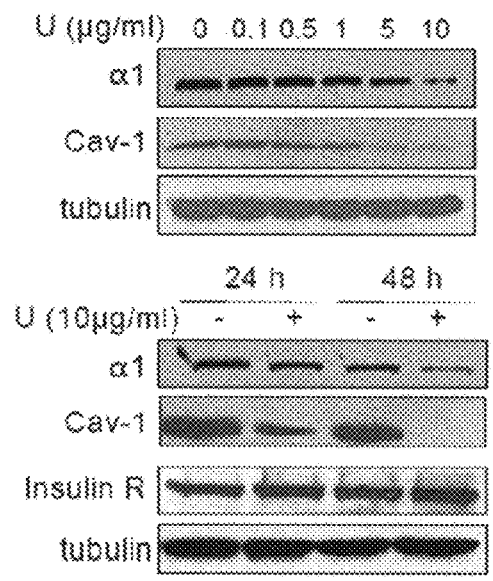
FIG. 3B. Representative Western blot from three independent experiments shows the effect of U18666A on Na/K-ATPase α1, caveolin-1 and α-tubulin after cells were treated for 48 h (upper panel). Representative Western blot from three independent experiments shows the effect of U18666A on the protein levels of Na/K-ATPase α1, insulin receptor β subunit and α-tubulin after cells were treated by U18666A for 24 h and 48 h, respectively (bottom). Scale bar: 20 μm. U, U18666A.

For example, either acute or chronic depletion of cellular cholesterol led to downregulation of the Na/K-ATPase (FIGS. 1 and 2). Moreover, an intracellular cholesterol trafficking inhibitor, U18666A that disrupted the trafficking between late endosomes/lysosomes and the plasma membrane, also downregulated cell surface Na/K-ATPase α1 (FIG. 3). As total cellular cholesterol showed no significant difference in the U18666A-treated cells, these results clearly indicate that it is the plasma membrane cholesterol content that regulates the cell surface Na/K-ATPase. This cholesterol depletion effect appeared to be specific to the Na/K-ATPase α1 because expression level of insulin receptor did not change (FIG. 3B).

Figure 1C:
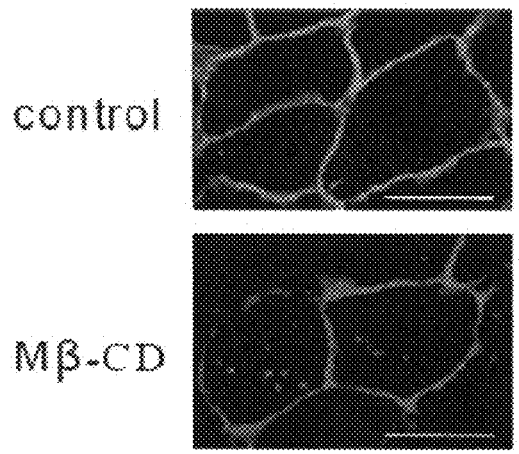
FIG. 1C. Representative confocal images of the cellular distribution of Na/K-ATPase α1 in the non-treated cells and Mβ-CD-treated cells are displayed.

At that point, it was of interest to examine how cholesterol depletion downregulated cell surface α1. Immunostaining revealed the redistribution of α1 from cell surface to intracellular compartments upon cholesterol depletion (FIGS. 1C and 3A). These observations indicated two possible scenarios: either newly synthesized α1 failed to transport to the cell surface or the surface α1 got endocytosed after surface cholesterol depletion. Subsequent studies pointed to the second scenario. Firstly, transcription of α1 appeared normal in U18666A-treated cells as the mRNA level was not altered. Secondly, general blockade of protein translation did not prevent redistribution of α1. Finally, α1 colocalized with both cholesterol and the late endosome marker, Rab7, after U18666A treatment (FIG. 4). Taken together, these data strongly indicate that the plasma membrane cholesterol pool regulates cell surface α1 content. Reduction of the plasma membrane cholesterol pool leads to endocytosis and downregulation of cell surface α1.

The Na/K-ATPase α1 Directly Interacts with Cholesterol and the Cholesterol-Regulated α1 Endocytosis is Dependent on α1-Cholesterol Interaction.

The mutual regulation of membrane distribution between the Na/K-ATPase α1 and cholesterol as demonstrated in our previous study; the two ubiquitously expressed molecules may interact directly. Other studies revealed that membrane cholesterol content influences the activity of the Na/K-ATPase and one study even implied the direct binding between the Na/K-ATPase and cholesterol. However, there is lack of the direct evidence on this matter before this study. In the present invention, the inventors instead use a FRET analysis to address this issue and demonstrated that the purified pig kidney Na/K-ATPase directly interacts with a cholesterol analog, NBD-cholesterol (FIG. 5). The inventors further located the cholesterol-binding site within NT of the α1 subunit and showed that the CRAC motif is essential for the binding (FIG. 5).

Figure 6A:
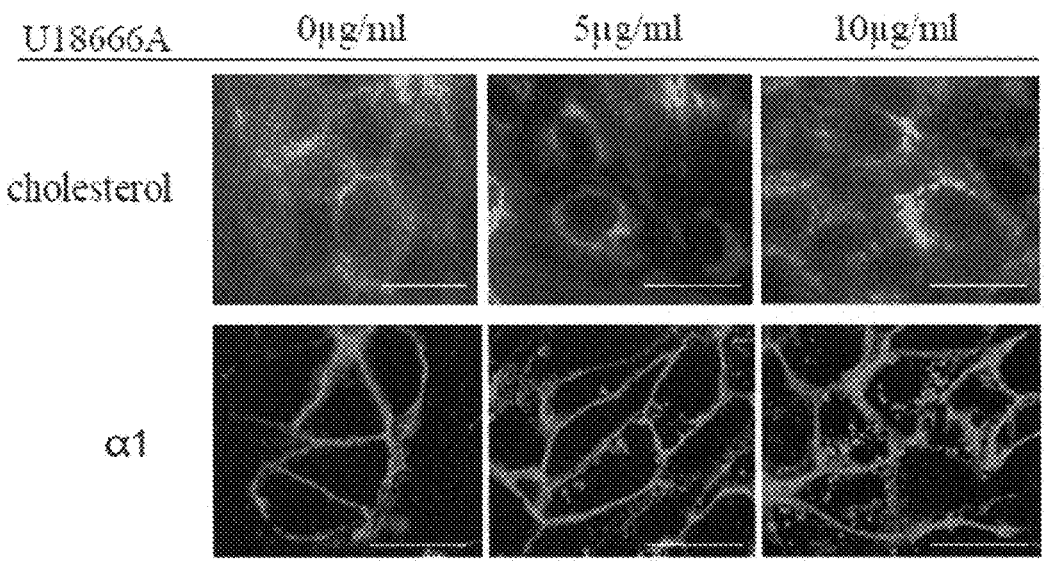
FIG. 6C A representative Western blot of four independent experiments is shown on the level of rat Na/K-ATPase α1 and α-tubulin in LLC-PK1 cells treated by 10 μg/ml U18666A and different doses of TAT-CRAC peptide for 24 h. Quantified data are presented below and expressed as Mean±S.E. **, p<0.01 compared to non-treated control.
Figure 6B:
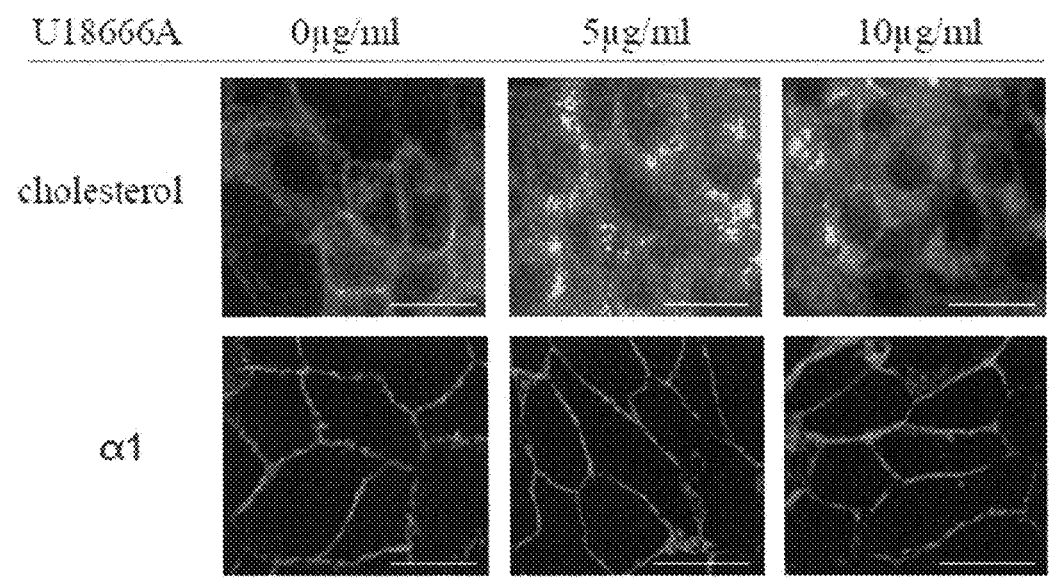

Interestingly, it appeared that the CRAC motif was important for cholesterol-regulated α1 endocytosis as disruption of this motif by site-directed mutagenesis rendered α1 insensitive to the plasma membrane cholesterol depletion. Furthermore, loading the cells with the membrane permeable CRAC peptide protected α1 from downregulation by U18666A, which is compatible with the above notion (FIG. 6). Because the CRAC mutant α1 localized within the plasma membrane normally (FIG. 6B), it is unlikely that α1-cholesterol interaction stabilizes cell surface Na/K-ATPase.

Instead, cholesterol may facilitate sorting of the Na/K-ATPase into the lipid raft, which mediates endocytosis of the Na/K-ATPase. It was proposed that lipid rafts, the assemblies of sphingolipids and cholesterol, were important for protein sorting during protein trafficking. Moreover, one type of lipid raft, caveolae was shown to concentrate the Na/K-ATPase and mediated its endocytosis. Considering the results in this study, it is conceivable that α1-cholesterol interaction is the key for proper sorting of the Na/K-ATPase into the lipid rafts like caveolae and subsequent endocytosis in response to various signals.

The Na/K-ATPase α1 as a Potential Plasma Membrane Cholesterol Sensor.

As an essential molecule to all mammalian cells, cholesterol level is tightly regulated by the cells. The most studied cellular cholesterol regulation machinery including HMG-CoA reductase and SCAP-SREBP2 complex reside in the ER membrane and their protein abundance and activity rely on the ER cholesterol pool. However, most of the cellular cholesterol localizes and functions in the plasma membrane and ER cholesterol pool is controlled by the plasma membrane cholesterol content. Thus, it was proposed that a plasma membrane cholesterol sensor exist and regulate cholesterol trafficking among the plasma membrane and internal membranes. The inventors investigated whether the Na/K-ATPase α1 is a plasma membrane cholesterol sensor. Firstly, like cholesterol, α1 is ubiquitously expressed in all mammalian cells and mainly localizes in the plasma membrane. Secondly, α1 controls cholesterol trafficking among the plasma membrane and intracellular compartments by regulating membrane trafficking of caveolin-1, α protein involved in intracellular cholesterol transport. Thirdly, cholesterol can interact with α1 and depletion of the plasma membrane cholesterol downregulates its cell surface level. Finally, reduction of α1 results in decrease in the plasma membrane cholesterol, which subsequently reduces ER cholesterol pool and activates SREBP2 pathway in vivo. Thus, a typical negative-feedback cycle is established for regulation of cellular cholesterol content by α1.

The Na/K-ATPase in NPC1 Disease.

The NPC1 disease is characterized by accumulation of intracellular cholesterol within the late endosomes/lysosomes, which is believed to be due to a defect of the cholesterol trafficking between internal membranes and the plasma membrane. But the major problem of the disease is the massive neuronal cell death in the central nervous system. However, it is not well understood how these two events are connected. On the other hand, the Na/K-ATPase is an essential molecule within the nervous system as it is one of the major forces to maintain the resting membrane potential. Recent studies have demonstrated that it also regulates cell growth and plays a key role in cell survival/cell death. Mutations in the Na/K-ATPase a subunit was linked to neurodegeneration. Because the treatment of U18666A to the cells mimics the phenotype of the NPC1 disease, downregulation of the Na/K-ATPase α1 by U18666A led us to investigate the α1 expression level in the NPC1 animal model. Interestingly, the inventors discovered that the α1 level was decreased in both the brain and liver of the NPC1 mutant mice (FIG. 7). This phenomenon seemed to be specific to the α1 molecule since another plasma membrane signaling protein, insulin receptor expression level was not affect by either U18666A or NPC1 mutant (FIGS. 3 and 7).

Figure 7A:
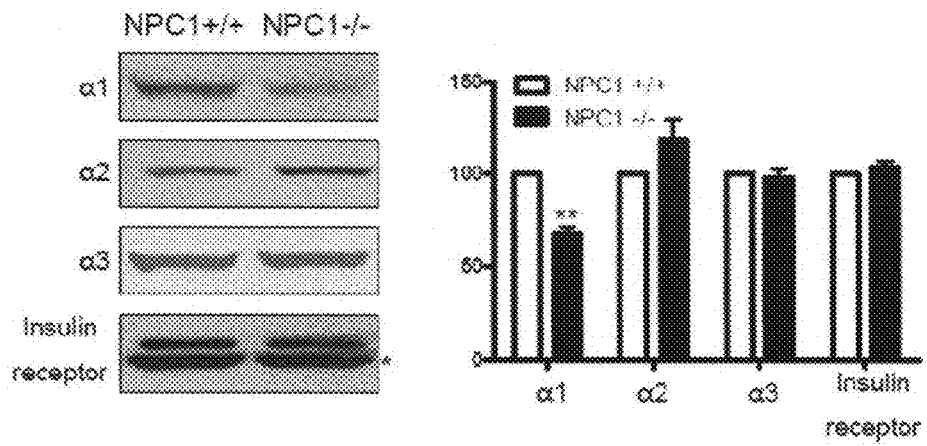
FIG. 7A. Representative Western blots show the effect of NPC1 knockout on brain Na/K-ATPase α1, α2, α3, and insulin receptor β subunit. The asterisk beside the lower band in insulin receptor blot denotes a non-specific band.

Furthermore, the levels of other two α isoforms (α2 and α3) in the NPC1 brain did not show significant difference (FIG. 7A). Thus, specific downregulation of α1 in the NPC1 brain has offered a new potential explanation for the link between intracellular cholesterol accumulation and neurodegeneration. This improves our knowledge on the cellular cholesterol metabolism and also facilitates new drug development with the Na/K-ATPase α1 as a novel target for the treatment of the neurodegenerative diseases.

Depletion of Plasma Membrane Cholesterol Results in Downregulation of the Na/K-ATPase α1 in LLC-PK1 Cells.

Previous studies have revealed that depletion of either cellular cholesterol or the Na/K-ATPase redistributes caveolin-1 to the perinuclear regions and cholesterol depletion redistributes Na/K-ATPase α1 out of the caveolae domain. The inventors investigated whether a change in cellular cholesterol level affects expression and distribution of the Na/K-ATPase, which regulates proper cellular caveolin-1 distribution. First, cells were treated with a cholesterol depletion drug, methyl β-cyclodextrin (Mβ-CD). Because of its high affinity for cholesterol, Mβ-CD is able to specifically extract cholesterol from the plasma membrane, which dramatically lowers cell surface cholesterol pool and redistributes caveolin-1. Moreover, previous work from the inventors' lab demonstrated that treatment of LLC-PK1 cells with 10 mM Mβ-CD for 30-60 minutes at 37° significantly lowered plasma membrane cholesterol pool. Therefore, the inventors used the same condition in these studies.

After Mβ-CD treatment to deplete cellular cholesterol, the inventors washed the drug off and replenished cellular cholesterol by incubating the cells in serum-free medium. Then, at different time points the inventors collected cell lysates and checked for proteins and cholesterol level. As shown in FIG. 1A, depletion of cellular cholesterol by Mβ-CD resulted in ~40% decrease in α1 level. Interestingly, Mβ-CD treatment led to similar decrease in cellular cholesterol level (FIG. 1B). 6 hours after cell recovery, both α1 and cholesterol remained at similar low levels suggesting that it took longer time for the cells to recover. However, 24 hours after cell recovery both α1 and cholesterol levels returned to control levels (FIGS. 1A and 1B). It should be noted that alterations in both α1 and cholesterol levels showed similar patterns during cholesterol depletion and repletion, which indicated that cellular α1 level was positively correlated to cholesterol level. Moreover, the cholesterol depletion effect on α1 expression was not a general effect on all the membrane proteins because expression of another plasma membrane protein, insulin receptor, was unchanged during cholesterol depletion and repletion (FIGS. 1A and 1B). To further confirm the result, the inventors performed α1 immunostaining after cholesterol depletion by Mβ-CD. Consistent with the Western blot data, the inventors detected lower α1 signals from the plasma membrane in Mβ-CD treated cells. Moreover, the inventors observed many intracellular α1 signals in Mβ-CD treated cells suggesting that cholesterol depletion led to α1 redistribution to intracellular compartments (FIG. 1C). The data above indicated that acute cholesterol depletion downregulated plasma membrane α1 level. To test whether chronic cholesterol depletion had the similar effect, the inventors next cultured the cells in either normal culture medium (DMEM plus serum) as control medium, serum-free medium (DMEM only) or lipoprotein-free medium (DMEM plus lipoprotein-free serum) for 48 hours. As expected, culturing the cells in both cholesterol-depleted media resulted in reduction in cellular cholesterol level (FIG. 2A). Accordingly, α1 levels were decreased in cells cultured in both of the cholesterol-depleted media (FIG. 2B). Furthermore, both α1 and cholesterol levels showed similar percentage of reduction in lipoprotein-free medium suggesting again that α1 level was positively correlated to cellular cholesterol level.

To further establish that it was the cell surface cholesterol pool that regulated plasma membrane α1, the inventors treated the cells with an intracellular cholesterol trafficking inhibitor, U18666A. The U compound is an amphiphile that disrupts intracellular cholesterol trafficking between internal membranes and cell surface, which leads to accumulation of cholesterol within late endosomes/lysosomes mimicking the phenotype of NPC1 mutant cells. Treatment of LLC-PK1 cells with U18666A led to redistribution of free cholesterol from the plasma membrane to intracellular compartments. The α1 signals were reduced in the plasma membrane but increased in the intracellular compartments, correlated to the pattern of cholesterol distribution (FIG. 3A).

Furthermore, downregulation of α1 expression by U18666A was both dose and time-dependent (FIG. 3B). Similar to cholesterol depletion, the effect of U compound on α1 expression appeared not to be a general effect on all plasma membrane proteins as insulin receptor content remained undisturbed after U18666A treatment (FIG. 3B).

Figure 3C:
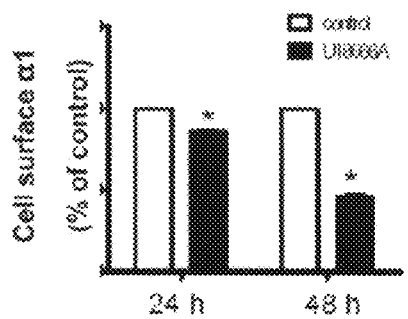
FIG. 3C. Cell surface Na/K-ATPase were quantified by 3H-ouabain binding.

Finally, to verify that U18666A downregulated cell surface α1, the inventors conducted a 3H-ouabain binding assay. The result confirmed that reduction of plasma membrane cholesterol led to downregulation of cell surface α1 (FIG. 3C). Finally, consistent with the notion that surface α1 regulates trafficking and expression of caveolin-1, U18666A also downregulated caveolin-1 protein level (FIG. 3B). Taken together, the data provide that α1 protein level is regulated by the plasma membrane cholesterol level.

Depletion of Plasma Membrane Cholesterol Leads to Endocytosis of the Na/K-ATPase α1.

Figure 4A:
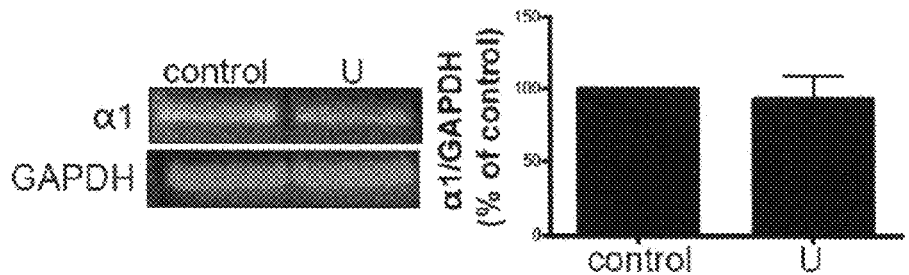
FIG. 4A. LLC-PK1 cells were treated with 10 μg/ml U18666A for 24 h. Total RNA was extracted and quantitative RT-PCR was performed to probe α1 and GAPDH mRNA as described herein. Data were from three independent experiments.

To explore the molecular mechanism underlying the effect of plasma membrane cholesterol depletion on α1 distribution and expression, the inventors conducted the following experiments. First of all, one possible explanation for the α1 down-regulation was that plasma membrane cholesterol depletion decreased α1 synthesis. To test this possibility, the inventors extracted total mRNA from control and U18666A-treated cells and conducted a quantitative PCR analysis. As shown in FIG. 4A, α1 mRNA level showed no difference compared to control, which suggested that plasma membrane cholesterol depletion may not affect α1 de novo synthesis.

Another possibility was that it disrupted normal trafficking of the newly synthesized α1 from endoplasmic reticulum to the plasma membrane. As a result, they got stuck in certain intracellular compartments since the inventors observed more intracellular α1 signals from Mβ-CD and U18666A treated cells (FIGS. 1C and 3A).

Figure 4B:
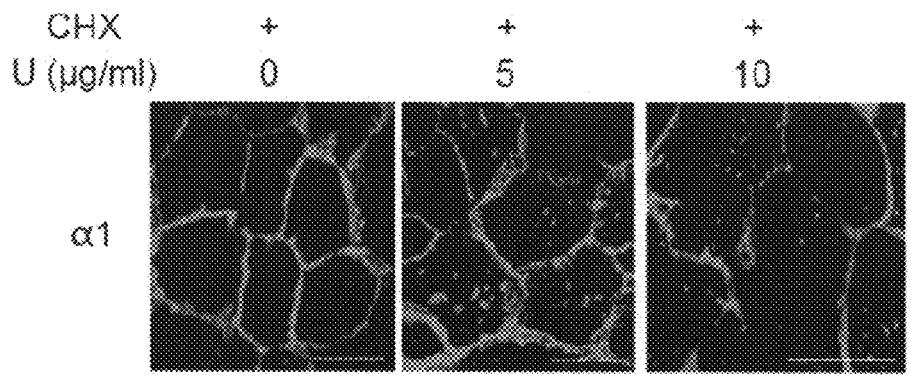
FIG. 4B. LLC-PK1 cells were treated with cycloheximide, 10 μg/ml for 1 h before exposed to different doses of U18666A for 24 h. Cells were then fixed and immunostained for Na/K-ATPase α1. Representative confocal images are shown. CHX, cycloheximide. U, U18666A.
Figure 4C:
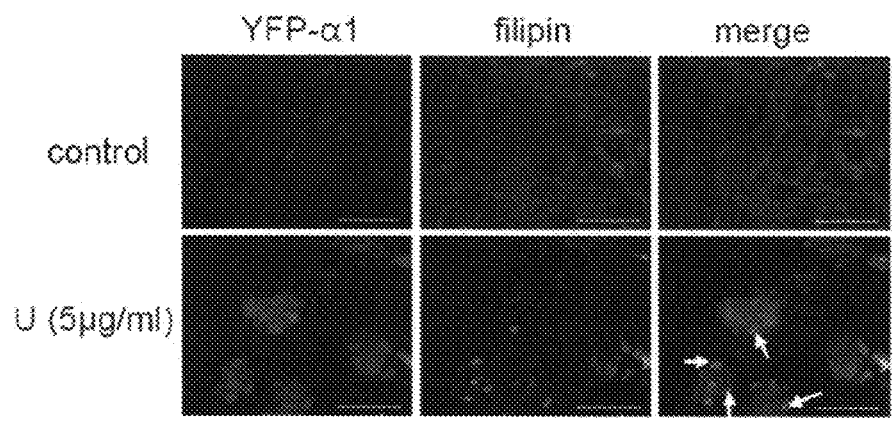
FIG. 4C. LLC-PK1 cells were transfected with YFP-α1 for 24 h before exposed to 5 μg/ml U18666A for another 24 h. Cells were fixed and stained with filipin for cholesterol. Representative confocal images of YFP-α1, cholesterol and merged figures are shown. Arrows point to the colocalization of YFP-α1 and cholesterol. The same experiments were repeated at least three times. Scale bar: 20 μm.

To test this possibility, the inventors treated the cells with a protein synthesis inhibitor, cycloheximide, before addition of U18666A to the cells. As shown in FIG. 4B, blockade of protein de novo synthesis by cycloheximide did not prevent U18666A-induced α1 redistribution to the intracellular compartments. This result indicated that U18666A may induce internalization of the cell surface α1. Because U18666A treatment led to accumulation of cholesterol in the intracellular compartments as well (FIG. 3A), the inventors next checked whether α1 and cholesterol were stuck in the same cellular compartments. The staining protocol of free cholesterol required different fixation reagent from that of α1, and it was not possible to look at both cholesterol and endogenous α1 in the same view. In order to solve that problem, the inventors transfected LLC-PK1 cells with YFP-α1 followed by U18666A treatment and cholesterol staining. The results demonstrate that most of the internalized α1 colocalized with free cholesterol after U18666A treatment (FIG. 4C, arrows pointing to the colocalization areas). According to the literature, U18666A treatment leads to free cholesterol accumulation in late endosomes/lysosomes. Therefore, the inventors investigated whether α1 was endocytosed and accumulated within late endosomes/lysosomes together with cholesterol. The inventors transiently transfected LLC-PK1 cells with RFP tagged Rab7, a late endosomes/lysosomes marker, before addition of U18666A.

Figure 4D:
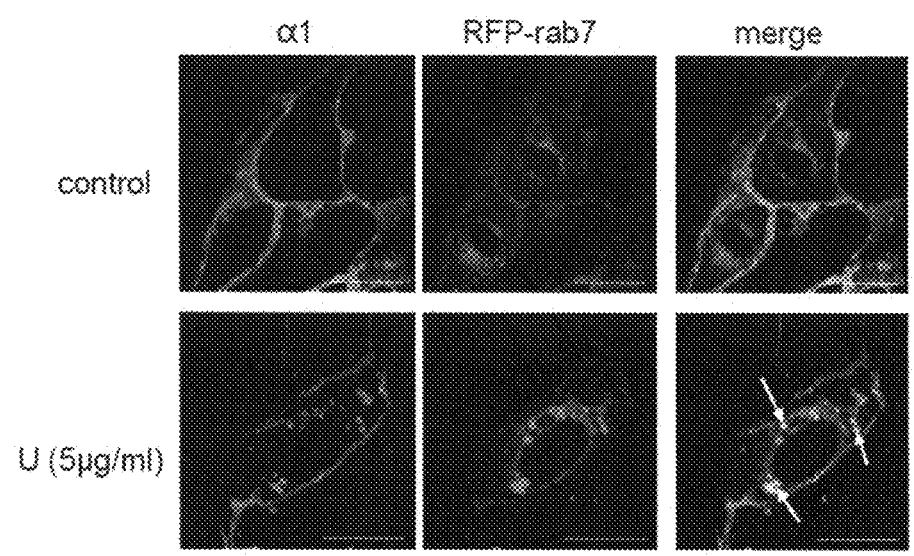
FIG. 4D. LLC-PK1 cells were transfected with RFP-rab7 for 24 h before exposed to 5 μg/ml U18666A for 24 h. Afterwards, cells were fixed and immunostained with Na/K-ATPase α1. Representative confocal images of α1 staining, RFP-rab7 and merged figures are shown. Arrows point to the colocalization of α1 and RFP-rab7. The same experiments were repeated at least three times. Scale bar: 20 μm.

As shown in FIG. 4D, in non-treated control cells most of the resided in the plasma membrane and no colocalization between α1 and Rab7 was detected. However, U18666A treatment led to massive intracellular α1 accumulation, most of which clearly colocalized with the Rab7 signals (arrows pointing to the colocalization areas). This confirmed that α1 accumulates within late endosomes/lysosomes upon U18666A treatment. Taken together, depletion of plasma membrane cholesterol by blocking its intracellular trafficking in LLC-PK1 cells not only induces endocytosis of α1 but also results in accumulation of α1 in the late endosomes/lysosomes.

The Na/K-ATPase α1 is able to Interact With Cholesterol Directly in Vitro via the N-terminal Cholesterol-binding Motif. As the inventors previously demonstrated, the Na/K-ATPase α1 in the plasma membrane regulated cellular cholesterol distribution. On the other hand, the data in the current study showed that the plasma membrane cholesterol also regulated membrane distribution of the Na/K-ATPase α1. Thus, the inventors investigated whether the two ubiquitously expressed molecules interact to each other directly. To test this proposition, the inventors first acquired purified Na/K-ATPase within membrane fragments from pig kidney outer medullar using a well-established method.

Figure 5A:
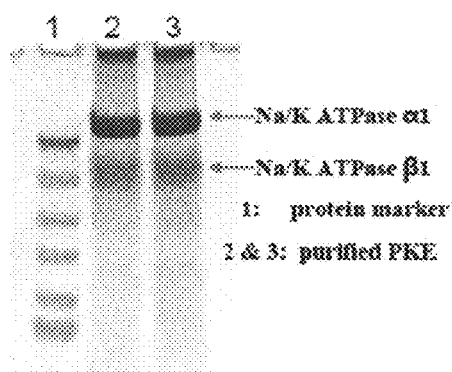
FIG. 5A. SDS-PAGE gel of PKE samples shows two bands, Na/K-ATPase α1 and β1, as indicated by the arrows.

To make sure the method worked efficiently the purified pig kidney enzyme (PKE) samples were run on the SDS-PAGE gel and stained the gel with Coomassie Blue solution. As shown in FIG. 5A, two bands with the corresponding sizes of the Na/K-ATPase α1 and β1 were detected in the gel.

Further Western blot analysis confirmed that the upper band represented the α1 subunit and the bottom band β1 subunit (data not shown).

Figure 5B:
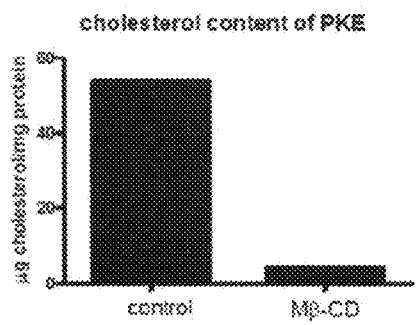
FIG. 5B. PKE was treated with 10 mM Mβ-CD or 10 mM Mβ-CD/1 mM cholesterol at 4° C. for 1 h. Cholesterol content in PKE subjected to different treatment was measured.
Figure 5C:
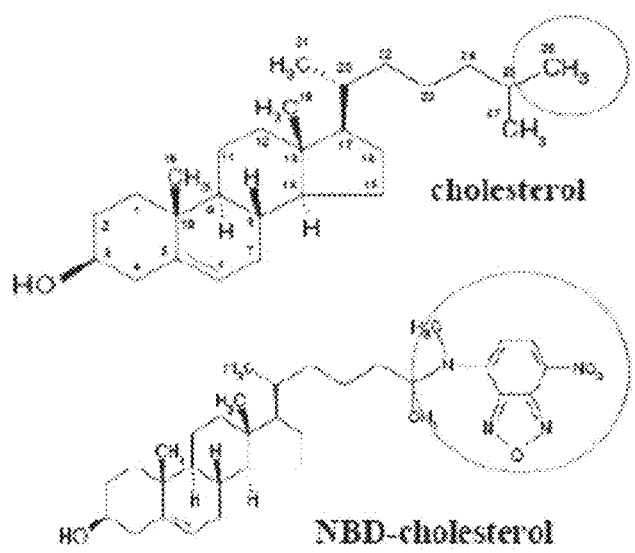
FIG. 5C. The schematic structures of cholesterol and NBD-cholesterol. Mβ-CD treated PKE (200 nM) was incubated with different doses of NBD-cholesterol. NBD signals FIG. 5D or FRET signals FIG. 5E were detected at 530 nm with excitation at 473 nm or 295 nm. A representative dose-dependent saturation curve of three independent experiments is shown. NBD-CH, NBD-cholesterol. 62.5 nM NBD-cholesterol was incubated with different doses of Mβ-CD treated PKE. NBD signals FIG. 5F or FRET signals FIG. 5G were detected at 530 nm with excitation at 473 nm or 295 nm. A typical dose-dependent saturation curve of three independent experiments is shown.
Figure 5D:
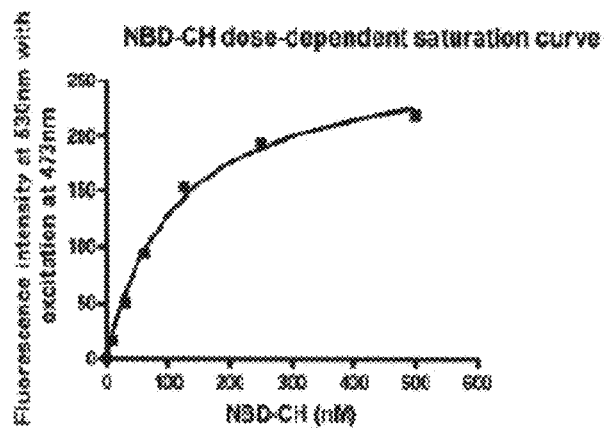
FIG. 5. NBD-Cholesterol Directly Interacts with Purified Na/K-ATPase. Purified Na/K-ATPase membrane samples (PKE) were prepared from pig kidney medulla.
FIG. 5H. GST and GST-tagged proteins were purified by GST pull-down assay. Purified proteins were subjected to SDS-PAGE electrophoresis and stained by Coomassie Blue. A representative Coomassie Blue stained gel is shown.
FIG. 5I. 62.5 nM NBD-cholesterol incubated with different doses of the purified proteins. FRET signals were detected at 530 nm with excitation at 295 nm. A typical dose-dependent saturation curve of three independent experiments is shown.
FIG. 5J. 100 nM purified proteins were incubated with different doses of NBD-cholesterol. FRET signals were detected at 530 nm with excitation at 295 nm. A typical dose-dependent saturation curve of three independent experiments is shown.
FIG. 5K. 100 nM PKE were mixed with 30 nM NBD-cholesterol, then different doses of cholesterol were added to compete for NBD-cholesterol binding to PKE. FRET signals were shown as a results of increase of the cholesterol doses FIG. 6. Cholesterol/α1 Interaction Is Required for Cholesterol-Regulated α1 Membrane Trafficking and Expression. Wild type rat α1-rescued cells FIG. 6A or cholesterol binding domain mutant rat α1-rescued cells FIG. 6B were treated by different doses of U18666A compound for 24 h and stained with filipin (upper panels) and Na/K-ATPase α1 (bottom panels). Scale bar: 20 μm.
Figure 5E:
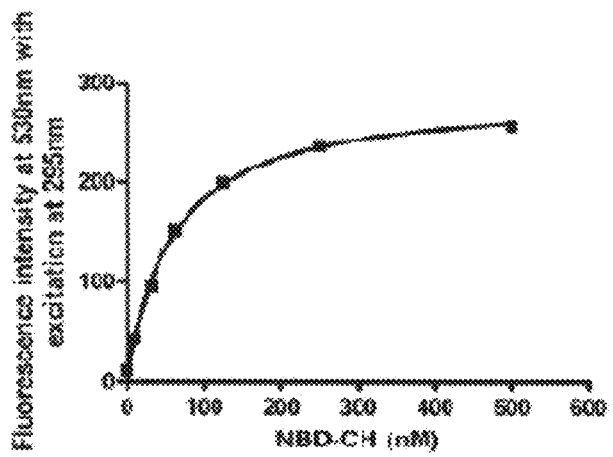
Figure 5F:
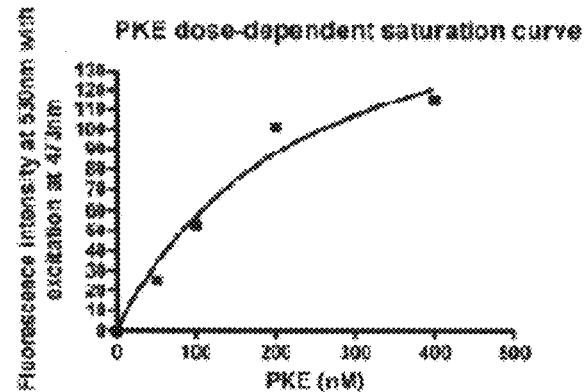
Figure 5G:
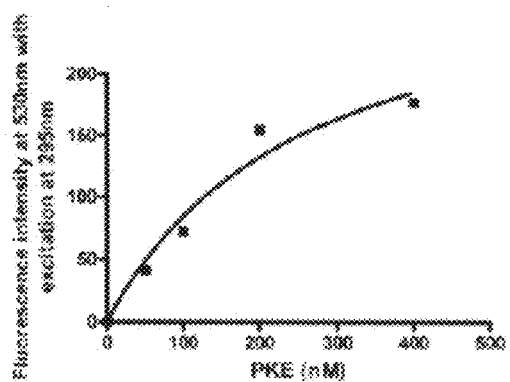

As the purified membrane fragments contained large amount of cholesterol, which may already saturated binding sites on the Na/K-ATPase, most of the cholesterol content was extracted by Mβ-CD (FIG. 5B). To study the binding between the Na/K-ATPase and cholesterol, a cholesterol analogue, 25-[N-[(7-nitro-2-1,3-benzoxadiazol-4-yl)methyl]amino]-27-norcholesterol (NBD cholesterol), was used for the binding assay. NBD-cholesterol was used for the study of protein-cholesterol interaction before. Unlike cholesterol, NBD-cholesterol is able to emit fluorescence signals that peak at ~530 nm when excited at 473 nm because of the replacement of the methyl group at C25 position with an NBD group (FIG. 5C). In the aqueous solution, its fluorescence is largely quenched. However, when it binds to a protein and is exposed to a hydrophobic environment, the fluorescence signals will increase. Moreover, it has much higher critical micelle concentration (~650 nM) than that of the cholesterol (30 nM) so that higher concentrations of the NBD-cholesterol can be used during the binding assay. 200 nM PKE were incubated with different doses of NBD-cholesterol and measured NBD fluorescence signal, and an NBD-cholesterol dose-dependent saturation curve (FIG. 5D) was observed. The Kd value is 100 nM-200 nM. Cholesterol competed the binding between NBD-cholesterol and the purified PKE (FIG. 5K).

To further confirm that the results represented lipid-protein interaction instead of lipid-lipid interaction, the inventors measured fluorescence resonance energy transfer (FRET) signals. When NBD-cholesterol binds to a protein, the tryptophan amino acid can be excited at 295 nm and emits at ~350 nm, which overlaps with the excitation spectral of the NBD-cholesterol. After incubating PKE with NBD-cholesterol and exciting Trp at 295 nm, the inventors detected an NBD-cholesterol dose-dependent saturation curve of the FRET signals at 530 nm (FIG. 5E). To confirm the results, the inventors incubated 62.5 nM NBD-cholesterol with different concentrations of PKE. Consistent with the previous experiment, incubation of NBD-cholesterol with PKE produced PKE dose-dependent saturation curve of both NBD signals (FIG. 5F) and FRET signals (FIG. 5G). Taken together, the observations indicate that purified Na/K-ATPase is able to directly interact with NBD-cholesterol in vitro.

To further dissect the cholesterol-binding site in the Na/K-ATPase, the inventors searched the literature and discovered that a cholesterol recognition/interaction amino acid sequence and consensus pattern (CRAC) was identified in most of the known cholesterol-binding proteins. Following studies further revealed that CRAC was responsible for cholesterol-binding and mutating the key amino acid Tyr in the middle of CRAC completely abolished cholesterol-binding affinity. As the inventors searched the primary sequence of the human Na/K-ATPase α1, it was found that there is one CRAC (Leu51-Arg61) within the N-terminus domain (NT) and the CRAC motif is highly conserved among mammalian species.

Figure 5H:
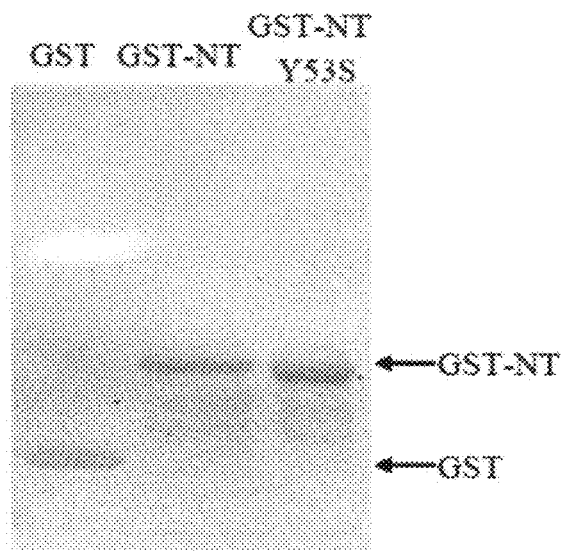
Figure 5I:
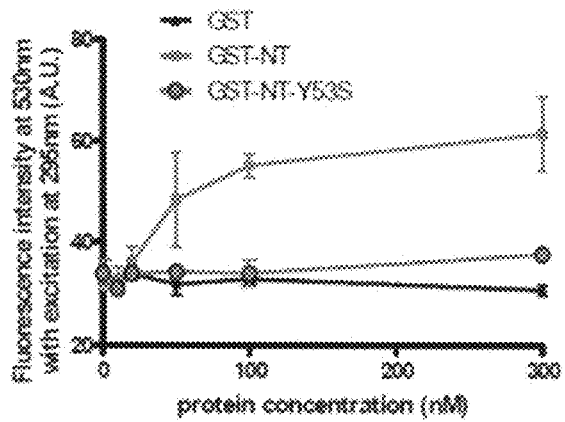
Figure 5J:
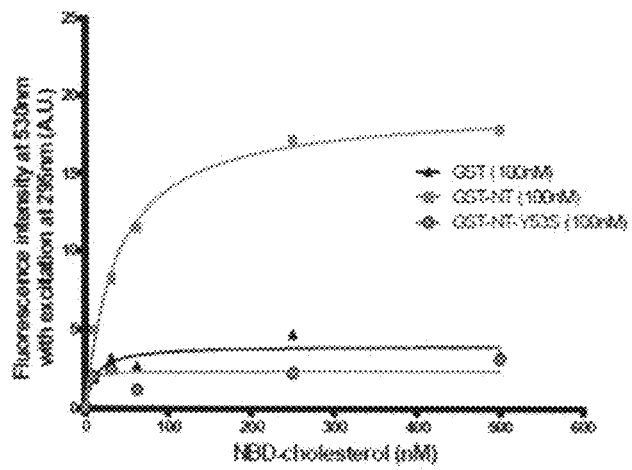
Figure 5K:
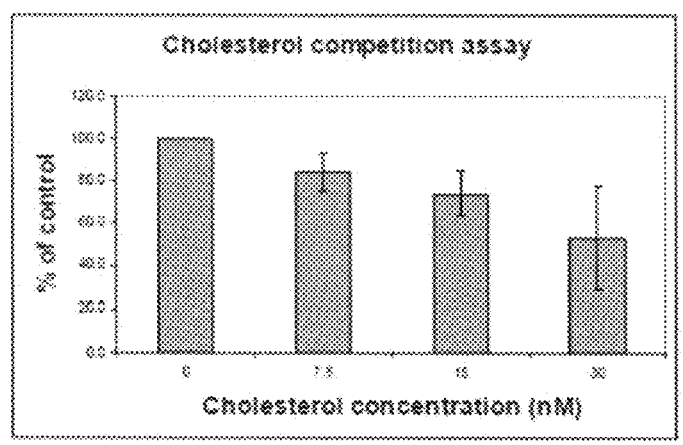

To test whether NT was responsible for Na/K-ATPase-cholesterol interaction, the inventors first attached a glutathione-S-transferase (GST) tag to NT peptide and purified GST-NT via GST pull-down assay (FIG. 5H). Then, NBD-cholesterol binding assay as in FIG. 5E was conducted. As shown in FIGS. 5I and 5J, while GST itself induced no FRET signal, GST-NT induced dose-dependent saturation FRET signal curve suggesting that NT had cholesterol-binding affinity. Furthermore, the inventors mutated the amino acid Tyr53 to Ser53 in the middle of the CRAC and performed the same NBD-cholesterol binding assay. Interestingly, the mutant NT-Y53S displayed no cholesterol-binding affinity. This indicates that the CRAC in the NT is responsible for cholesterol-binding.

The CRAC of Na/K-ATPase α1 is Essential for Cholesterol-Regulated α1 Membrane Trafficking.

The data in the previous section demonstrated that the NT of Na/K-ATPase α1 is capable of interacting with cholesterol via CRAC in vitro. Thus, it was of interest to explore whether the CRAC plays a role in cholesterol depletion-induced α1 endocytosis. Firstly, the inventors treated wild-type rat α1 rescued-cells, AAC-19, with U18666A and stained both α1 and cholesterol. As shown in FIG. 6A, the wild-type rat α1 in the LLC-PK1 cells behaved like endogenous pig α1 (FIG. 3A). Depletion of plasma membrane cholesterol led to endocytosis of α1 in a dose-dependent manner.

Figure 6C:
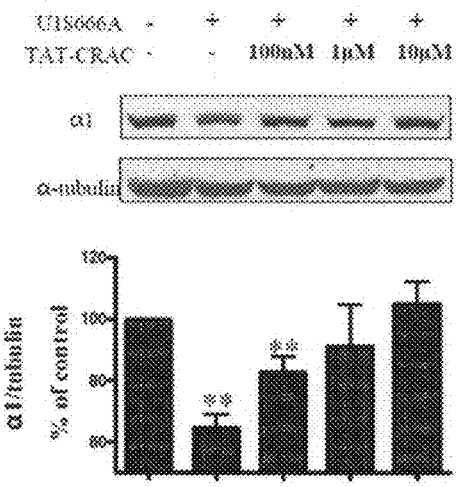

Next, the inventors mutated the essential Tyr55 in the rat α1 CRAC (corresponds to the Tyr53 in pig α1) to Ser55 by a site-directed mutagenesis method and generated the stable mutant rat α1-rescued cell line (PY-17-Y55S). Once the cell line was established, the inventors did the same experiment as on AAC-19 cells. Interestingly, contrary to the wild-type rat α1, the Y55S mutant rat α1 showed no obvious endocytosis in response to U18666A treatment (FIG. 6B). To confirm the findings, the inventors had the CRAC synthesized with a positively charged leader peptide, HIV-TAT, tagged to the N-terminus of CRAC so that the TAT-CRAC peptide was cell permeable. Theoretically, loading of the TAT-CRAC peptide into the cells may interrupt the binding between endogenous α1 and cholesterol by competitive inhibition. As shown in FIG. 6C, the TAT-CRAC peptide rescued the α1 downregulation effect by U18666A in a dose-dependent manner. Taken together, the cholesterol-regulated Na/K-ATPase α1 membrane trafficking is dependent on the cholesterol-α1 interaction.

The Na/K-ATPase α1 is Downregulated in the Livers and Brains of NPC1 Mutant Mice.

As mentioned before, the amphiphile compound U18666A treatment on the cells leads to NPC1-like phenotype. Downregulation of the Na/K-ATPase α1 in U18666A-treated cells prompted us to check whether this effect was physiologically related to NPC1 disease. Because the NPC1 disease is a lipid storage disorder and shows prominent neurodegeneration in the central nervous system, the inventors focused on two most relevant organs, brain and liver. As shown in FIG. 7A, the Na/K-ATPase α1 protein expression level was decreased for about 40% in the NPC1−/− mouse brains, consistent with our previous in vitro data. Because brain cells express three isoforms of the a subunit, the inventors checked the protein level of α2 and α3. While α2 level increased a little but not significantly, α3 level showed no difference in control and NPC1 mouse brains.

Figure 7B:
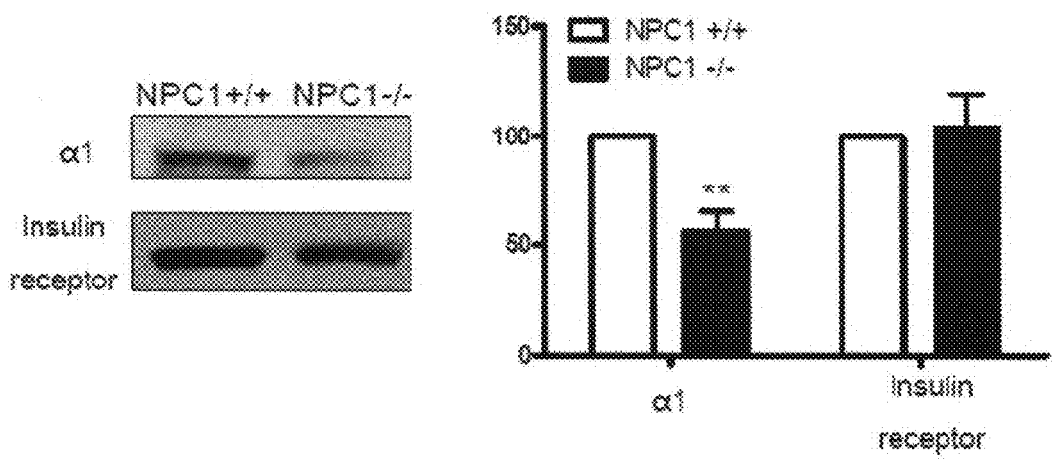
FIG. 7B. Representative Western blots on Na/K-ATPase α1 and insulin receptor β of liver samples from NPC1$^{+/+}$ and NPC1$^{-/-}$ mice are shown. All Western results were quantified from 5 NPC1$^{+/+}$ and 5 NPC1$^{-/-}$ mice, shown in the right panels and expressed as Mean±SE. **, p<0.01.

Furthermore, consistent with previous data, insulin receptor protein level was not altered in the NPC1 mouse brains (FIG. 7A). Thus, it appears that the cholesterol trafficking defect in NPC1 disease specifically affects α1 expression. Finally, it was discovered that α1 level was also decreased to half in the NPC1 mouse hepatic cells while insulin receptor showed no obvious difference (FIG. 7B). However, the α1 downregulation effect appears to be organ-specific as α1 level in the heart and kidney did not display significant difference.

EXAMPLES

Example 1

Materials

Cell culture media, fetal bovine serum and trypsin were purchased from Invitrogen. The antibodies and their sources are as follows: The mouse monoclonal anti-Na/K-ATPase α1 antibody (a6F) for Western blot analysis was purchased from the Developmental Studies Hybridoma Bank at the University of Iowa. The mouse monoclonal anti-Na/K-ATPase α1 antibody for immunocytochemistry was from Upstate Biotechnology Inc. (Lake Placid, N.Y.). The mouse monoclonal anti-insulin receptor B subunit antibody, the rabbit polyclonal anti-caveolin-1 antibody, the mouse monoclonal anti-a-tubulin antibody and all secondary antibodies were from Santa Cruz Biotechnology (Santa Cruz, Calif.). The rabbit polyclonal anti-Na/K-ATPase a2 antibody (HERED) and the rabbit polyclonal anti-Na/K-ATPase a3 antibody were gifts from Dr. Thomas A. Pressley in Texas Tech University. Optitran nitrocellulose membrane was from Schleicher & Schuell. Enhanced chemiluminescence SuperSignal kit was purchased from Pierce. Mβ-CD, cycloheximide and filipin were obtained from Sigma-Aldrich (St. Louis, Mo.). The U18666A compound was from Cayman Chemical (Ann Arbor, Mich.). Lipofectamine 2000 was purchased from Invitrogen. The Amplex Red Cholesterol Assay Kit was purchased from Molecular Probes, Inc. (Eugene, Oreg.). [3H] Ouabain was from PerkinElmer Life Sciences (Waltham, Mass.). NBD-cholesterol was from Avanti Polar Lipids (Alabaster, Ala.). The QuikChange site-directed mutagenesis kit was obtained from Stratagene (La Jolla, Calif.). The TAT-CRAC peptide was synthesized with high purity (>95%). Identity and purity were confirmed by high performance liquid chromatography mass spectroscopy.

Cell Culture

The LLC-PK1 cells were obtained from American Type Culture Collection. The rat α1-rescued Na/K-ATPase α1 knockdown cells (AAC-19) and the caveolin-binding motif mutant rat α1 rescued Na/K-ATPase α1 knockdown cells (mCBM) were derived from LLC-PK1 cells as previously described. All cells were cultured in Dulbecco's modified Eagle's medium (DMEM) containing 10% fetal bovine serum, penicillin (100 units/ml)/streptomycin (100 μg/ml) in a 5% CO2-humidified incubator. After cells reached 100% confluence, they were serum-starved for 24 hours and used for experiments unless indicated otherwise.

Plasmid Constructs and Transfection

The rat α1 CRAC mutant (Tyr55 to Ser55) was created by PCR-based site-directed mutagenesis on the pRc/CMV-a1AACm1 plasmid as generated previously. The Y55S mutant rat α1 knock-in cell line was then established using the same protocol described before. The pEYFP-α1 plasmid was generated as described previously. RFP-rab7 plasmid was requested from www.addgene.org. The preparation of plasmid constructs expressing GST fusion proteins were made from pGEX-4T-1 as previously described. GST-NT (Ala1-Ser160) and GST-NT-Y55S expression vectors were constructed based on sequence of pig kidney Na/K-ATPase α1 subunit. All constructs were verified by DNA sequencing. For transfection, cells were grown to about 70% confluence and transfected with the corresponding plasmids by Lipofectamine 2000 as described previously. Following experiments were performed 24 hours after transfection.

Experimental Animals

NPC1+/− mice in BALB/c genetic background were purchased from The Jackson Laboratory. NPC1+/+ and NPC1−/− mice were produced by mating two NPC1+/− mice. Genomic DNA was obtained from tail biopsies and used for PCR-based genotyping. All mice were kept in a 12-h dark/light cycle and fed standard chow ad libitum. All animal experiments were conducted among littermates. All procedures were approved by the Institutional Animal Care and Use Committee at the University of Toledo, Health Science Campus. All mice were sacrificed on 10 weeks old and organs including brain, liver, heart and kidney were carefully dissected and weighed. All tissues were immediately frozen in liquid nitrogen and stored at −80. for Western blot analysis.

Example 2

Methods

Cellular Cholesterol Depletion of Mβ-CD and Recovery

LLC-PK1 cells were grown in 6 cm culture dish to 100% confluence and serum starved for 24 hours. Cells were then treated by 10 mM Mβ-CD for 1 hour. Next, Mβ-CD was removed and cells were allowed to recover in DMEM for 0, 6, 24 hours respectively before scraped down in RIPA buffer. Cell lysates were subject to protein assay and Western blot analysis.

Western Blot Analysis

Protein concentrations of cell lysates or tissue homogenates were measured by Protein Assay Kit from Bio-Rad (Hercules, Calif.). Equal amounts of protein were loaded onto the gel and separated on 10% SDS-PAGE, transferred to an Optitran membrane, and probed with corresponding antibodies. Protein signals were detected with an ECL kit. The density of the Western bands was quantified by the free software Image J.

Immunocytochemistry

Staining of the Na/K-ATPase α1 was performed as previously described. Briefly, cells were serum-starved for 24 hours and treated on coverslips. The cells were then fixed with ice-cold methanol for 30 min and blocked with Signal Enhancer from Invitrogen. Next, cells were incubated with a monoclonal anti-Na/K-ATPase α1 antibody at 4° C. overnight. After three washes with PBS, a secondary Alex 488-conjugated anti-mouse antibody was added and incubated at room temperature for 3 hours. The coverslip was washed, mounted and imaged with a Leica confocal microscope.

Cholesterol Assay and Filipin Staining

Cholesterol assay and filipin staining were performed as described in Chen et al., Regulation of intracellular cholesterol distribution by Na/K-ATPase. Journal Biological Chemistry, Volume 284, pages 14881-14890 (2009).

[3H]Ouabain Binding

[3H]Ouabain Binding was conducted as described in Tian et al., Changes in sodium pump expression dictate the effects of ouabain on cell growth, Journal of Biological Chemistry, 14921-1429 (2009).

Quantitative RT-PCR

The quantitative RT-PCR on mRNA levels of Na/K-ATPase α1 and GAPDH were performed as described in Tian et al., Changes in sodium pump expression dictate the effects of ouabain on cell growth, Journal of Biological Chemistry, 14921-1429 (2009).

NBD-Cholesterol Binding Assay

NBD-cholesterol Binding Assay was performed as described in Petrescu et al., Steroidogenic acute regulatory protein binds cholesterol and modulates mitochondrial membrane sterol doman dynamics, Journal Biological Chemistry, Volume 276, pages 36970-36982 (2001).

Purification of Na/K-ATPase and GST-Fused Proteins

Na/K-ATPase was purified from pig kidney outer medulla using the Jorgensen method. GST-fused proteins were expressed in *Escherichia coli* BL21 (Invitrogen) and purified by glutathione beads. Soluble GST-fused proteins were eluted from the glutathione beads with elution buffer (10 mM reduced glutathione, 0.1% Triton X-100, 50 mM Trish, pH 8.0). The eluted solution was dialyzed in the buffer containing 0.1% Triton X-100, 50 mM Tris-HCl, pH 8.0, to remove remnant glutathione.

Statistical Analysis

Data are given as mean±S.E. Statistical analysis was performed using the Student's t test and significance was accepted at p<0.05.

Example 3

Assay for Test Compositions which May Modulate Intracellular Cholesterol

The inventors extracted total mRNA from control and U18666A-treated cells and conducted a quantitative PCR analysis. As shown in FIG. 4A, α1 mRNA level showed no difference compared to control, which suggested that plasma membrane cholesterol depletion may not affect α1 de novo synthesis.

The inventors also treated the cells with a protein synthesis inhibitor, cycloheximide, before addition of U18666A to the cells, in a separate experiment. As shown in FIG. 4B, blockade of protein de novo synthesis by cycloheximide did not prevent U18666A-induced α1 redistribution to the intracellular compartments. This result indicated that U18666A may induce internalization of the cell surface α1. Because U18666A treatment led to accumulation of cholesterol in the intracellular compartments as well (FIG. 3A), the inventors next checked whether α1 and cholesterol were stuck in the same cellular compartments. The staining protocol of free cholesterol required different fixation reagent from that of α1, and it was not possible to look at both cholesterol and endogenous α1 in the same view. In order to solve that problem, the inventors transfected LLC-PK1 cells with YFP-α1 followed by U18666A treatment and cholesterol staining. The results demonstrate that most of the internalized α1 colocalized with free cholesterol after U18666A treatment (FIG. 4C, arrows pointing to the colocalization areas).

The inventors also transiently transfected LLC-PK1 cells with RFP tagged Rab7, a late endosomes/lysosomes marker, before addition of U18666A in a separate experiment. As shown in FIG. 4D, in non-treated control cells most of the resided in the plasma membrane and no colocalization between α1 and Rab7 was detected. However, U18666A treatment led to massive intracellular α1 accumulation, most of which clearly colocalized with the Rab7 signals (arrows pointing to the colocalization areas). This confirmed that α1 accumulates within late endosomes/lysosomes upon U18666A treatment.

Example 4

Assays for Test Compositions which May Modulate Plasma Membrane Cholesterol

First, cells were treated with a cholesterol depletion drug, methyl β-cyclodextrin (Mβ-CD). Because of its high affinity for cholesterol, Mβ-CD is able to specifically extract cholesterol from the plasma membrane, which dramatically lowers cell surface cholesterol pool and redistributes caveolin-1. Moreover, previous work from the inventors' lab demonstrated that treatment of LLC-PK1 cells with 10 mM Mβ-CD for 30-60 minutes at 37° significantly lowered plasma membrane cholesterol pool. Therefore, the inventors used the same condition in these studies.

After Mβ-CD treatment to deplete cellular cholesterol, the inventors washed the drug off and replenished cellular cholesterol by incubating the cells in serum-free medium. Then, at different time points the inventors collected cell lysates and checked for proteins and cholesterol level. As shown in FIG. 1A, depletion of cellular cholesterol by Mβ-CD resulted in ~40% decrease in α1 level. Interestingly, Mβ-CD treatment led to similar decrease in cellular cholesterol level (FIG. 1B). 6 hours after cell recovery, both α1 and cholesterol remained at similar low levels suggesting that it took longer time for the cells to recover. However, 24 hours after cell recovery both α1 and cholesterol levels returned to control levels (FIGS. 1A and 1B). It should be noted that alterations in both α1 and cholesterol levels showed similar patterns during cholesterol depletion and repletion, which indicated that cellular α1 level was positively correlated to cholesterol level. Moreover, the cholesterol depletion effect on α1 expression was not a general effect on all the membrane proteins because expression of another plasma membrane protein, insulin receptor, was unchanged during cholesterol depletion and repletion (FIGS. 1A and 1B).

To further confirm the result, the inventors performed α1 immunostaining after cholesterol depletion by Mβ-CD. Consistent with the Western blot data, the inventors detected lower α1 signals from the plasma membrane in Mβ-CD treated cells. Moreover, the inventors observed many intracellular α1 signals in Mβ-CD treated cells suggesting that cholesterol depletion led to α1 redistribution to intracellular compartments (FIG. 1C). The data above indicated that acute cholesterol depletion downregulated plasma membrane α1 level.

To test whether chronic cholesterol depletion had the similar effect, the inventors next cultured the cells in either normal culture medium (DMEM plus serum) as control medium, serum-free medium (DMEM only) or lipoprotein-free medium (DMEM plus lipoprotein-free serum) for 48 hours. As expected, culturing the cells in both cholesterol-depleted media resulted in reduction in cellular cholesterol level (FIG. 2A). Accordingly, α1 levels were decreased in cells cultured in both of the cholesterol-depleted media (FIG. 2B). Furthermore, both α1 and cholesterol levels showed similar percentage of reduction in lipoprotein-free medium suggesting again that α1 level was positively correlated to cellular cholesterol level.

To further establish that it was the cell surface cholesterol pool that regulated plasma membrane α1, the inventors treated the cells with an intracellular cholesterol trafficking inhibitor, U18666A. The U compound is an amphiphile that disrupts intracellular cholesterol trafficking between internal membranes and cell surface, which leads to accumulation of cholesterol within late endosomes/lysosomes mimicking the phenotype of NPC1 mutant cells. Treatment of LLC-PK1 cells with U18666A led to redistribution of free cholesterol from the plasma membrane to intracellular compartments. The α1 signals were reduced in the plasma membrane but increased in the intracellular compartments, correlated to the pattern of cholesterol distribution (FIG. 3A).

Furthermore, downregulation of α1 expression by U18666A was both dose and time-dependent (FIG. 3B). Similar to cholesterol depletion, the effect of U compound on α1 expression appeared not to be a general effect on all plasma membrane proteins as insulin receptor content remained undisturbed after U18666A treatment (FIG. 3B).

Finally, to verify that U18666A downregulated cell surface α1, the inventors conducted a 3H-ouabain binding assay. The result confirmed that reduction of plasma membrane cholesterol led to downregulation of cell surface α1 (FIG. 3C). Finally, consistent with the notion that surface α1 regulates trafficking and expression of caveolin-1, U18666A also downregulated caveolin-1 protein level (FIG. 3B).

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

We claim:

1. A method to affect cholesterol transport in a cell, comprising:
administering to the cell a composition of matter comprising an amino acid compound of 17 residues comprising at least ten consecutive amino acid residues of a cholesterol recognition/interaction amino acid sequence and consensus pattern (CRAC) sequence having SEQ ID NO:2, or conservative substitutions of the at least ten consecutive amino acid residues of SEQ ID NO:2, wherein the compound is capable of binding cholesterol and affecting sodium/potassium adenosine triphosphate synthase (Na/K ATPase) cholesterol-binding activity by antagonizing the CRAC domain on an α1 subunit of Na/K ATPase.

2. The method of claim 1, wherein Na/K ATPase cholesterol-binding activity is affected in a manner selected from the group consisting of: decreasing; increasing; eliminating; periodically disrupting; and periodically enhancing.

3. A method to ameliorate neurodegeneration due to pathogenic intracellular cholesterol accumulation in a cell in need of such amelioration, comprising: administering to the cell a composition of matter comprising an amino acid compound of 17 residues comprising at least ten consecutive amino acid residues of a cholesterol recognition/interaction amino acid sequence and consensus pattern (CRAC) sequence having SEQ ID NO:2, or conservative substitutions of the at least ten consecutive amino acid residues of SEQ ID NO:2, wherein the compound is capable of binding cholesterol and decreasing the cholesterol binding activity of sodium/potassium adenosine triphosphate synthase (Na/K ATPase) by antagonizing the CRAC domain in an α1 subunit of Na/K ATPase.

4. A method of treating Niemann Pick, type C1 disease, comprising: administering to the cell a composition of matter comprising an amino acid compound of 17 residues comprising at least ten consecutive amino acid residues of a cholesterol recognition/interaction amino acid sequence and consensus pattern (CRAC) sequence having SEQ ID NO:2, or conservative substitutions of the at least ten consecutive amino acid residues of SEQ ID NO:2, wherein the compound is capable of binding cholesterol and decreasing the ability of sodium/potassium adenosine triphosphate synthase (Na/K ATPase) to bind to cholesterol by antagonizing the CRAC domain of an α1 subunit of Na/K ATPase.

5. The method of claim 4, wherein the decrease is accomplished by inhibiting the CRAC domain of the α1 subunit of Na/K ATPase.

6. A method to identify compositions capable of treating cholesterol-related disease states, comprising
   a) contacting a test sample with a composition comprising an amino acid compound of 17 residues comprising at least ten consecutive amino acid residues or conservative substitutions of the at least ten consecutive amino acid residues of a cholesterol recognition/interaction amino acid sequence and consensus pattern (CRAC) domain in an α1 subunit of Na/K ATPase having SEQ ID NO:2; and
   b) identifying if step a) results in antagonizing the ability of cholesterol to bind to the CRAC domain of the α1 subunit of Na/K ATPase.

7. A method to identify compositions capable of treating at least one disease state, comprising
   a) contacting a test sample with a composition comprising an amino acid compound of 17 residues comprising at least ten consecutive amino acid residues or conservative substitutions of the at least ten consecutive amino acid residues of a cholesterol recognition/interaction amino acid sequence and consensus pattern (CRAC) domain in an α1 subunit of Na/K ATPase having SEQ ID NO:2; and
   b) identifying if step a) results in antagonizing the ability of cholesterol to bind to the CRAC domain of the α1 subunit of Na/K ATPase, wherein the disease state is selected from the group consisting of: NPC1; pathogenic lipid accumulation; vascular disease; heart attack; stroke; overweight; obesity; diabetes; metabolic syndrome; thyroid malfunction; medication side effect; atherosclerosis; heart failure; heart disease; Alzheimer's disease; Parkinson disease; Huntington disease; Tay Sachs disease and neurodegenerative disease.

8. A method to affect the trafficking and expression of caveolin-1 in a cell, comprising:
   administering to the cell, a composition of matter comprising an amino acid compound of 17 residues comprising at least ten consecutive amino acid residues of a cholesterol recognition/interaction amino acid sequence and consensus pattern (CRAC) sequence having SEQ ID NO:2, or conservative substitutions of the at least ten consecutive amino acid residues of SEQ ID NO:2, wherein the compound is capable of binding cholesterol and down-regulating plasma membrane α1 subunit of sodium/potassium adenosine triphosphate synthase (Na/K ATPase) the Na/K ATPase having the CRAC domain in an α1 subunit of Na/K ATPase.

9. A method to treat Niemann Pick, type C1 disease (NPC1 disease), comprising:
   administering to a subject having Niemann Pick, type C1 disease, a composition of matter comprising an amino acid compound of 17 residues comprising at least ten consecutive amino acid residues of a cholesterol recognition/interaction amino acid sequence and consensus pattern (CRAC) sequence having SEQ ID NO:2, or conservative substitutions of the at least ten consecutive amino acid residues of SEQ ID NO:2, wherein the compound is capable of binding cholesterol and altering expression of the α1 subunit of sodium/potassium adenosine triphosphate synthase (Na/K ATPase) the Na/K ATPase having the CRAC domain in an α1 subunit of Na/K ATPase so as to ameliorate the symptoms of NPC1 disease.

10. The method of claim 1, wherein the cell is a mammal cell.

11. The method of claim 3, wherein the cell is a mammal cell.

12. The method of claim 8, wherein the cell is a mammal cell.

13. The method of claim 10, wherein the mammal cell is selected from the group consisting of: liver cells; kidney cells; brain cells; nerve cells; pancreatic cells; lung cells; skin cells; heart cells; rodent cells; human cells; mouse cells; rat cells; guinea pig cells; dog cells; and, monkey cells.

14. The method of claim 11, wherein the mammal cell is selected from the group consisting of: liver cells; kidney cells; brain cells; nerve cells; pancreatic cells; lung cells; skin cells; heart cells; rodent cells; human cells; mouse cells; rat cells; guinea pig cells; dog cells; and, monkey cells.

15. The method of claim 12, wherein the mammal cell is selected from the group consisting of: liver cells; kidney cells; brain cells; nerve cells; pancreatic cells; lung cells; skin cells; heart cells; rodent cells; human cells; mouse cells; rat cells; guinea pig cells; dog cells; and, monkey cells.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Unknown
<220> FEATURE:
<223> OTHER INFORMATION: Description of Unknown: Na/K-ATPase
      peptide

<400> SEQUENCE: 1

Ser Thr Asn Cys Val Glu Gly Thr Ala Arg Gly Ile Val Val Tyr Thr
1               5                   10                  15

Gly Asp

<210> SEQ ID NO 2
<211> LENGTH: 17
<212> TYPE: PRT
<213> ORGANISM: Unknown
<220> FEATURE:
<223> OTHER INFORMATION: Description of Unknown: Na/K-ATPase
      CRAC peptide

<400> SEQUENCE: 2

Leu Asp Glu Leu His Arg Lys Tyr Gly Thr Asp Leu Ser Arg Gly Leu
1               5                   10                  15

Thr
```